(12) United States Patent
Kim et al.

(10) Patent No.: US 8,167,804 B2
(45) Date of Patent: May 1, 2012

(54) MEASUREMENT OF TISSUE ELASTIC MODULUS

(75) Inventors: Kang Kim, Ann Arbor, MI (US);
William F. Weitzel, Ypsilanti, MI (US);
Jonathan M. Rubin, Ann Arbor, MI (US); Congxian Jia, Ann Arbor, MI (US); Matthew O'Donnell, Seattle, WA (US); Theodore J. Kolias, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1246 days.

(21) Appl. No.: 11/866,000

(22) Filed: Oct. 2, 2007

(65) Prior Publication Data
US 2008/0081994 A1   Apr. 3, 2008

Related U.S. Application Data

(60) Provisional application No. 60/849,073, filed on Oct. 3, 2006.

(51) Int. Cl.
*A61B 8/00* (2006.01)
(52) U.S. Cl. ........ 600/438; 600/407; 600/437; 600/441; 600/448; 600/480; 600/481; 600/439
(58) Field of Classification Search .................. 600/407, 600/437–448, 481, 480
See application file for complete search history.

(56) References Cited

U.S. PATENT DOCUMENTS

| | | | | |
|---|---|---|---|---|
| 5,524,636 A * | 6/1996 | Sarvazyan et al. | ............ | 600/587 |
| 5,830,131 A * | 11/1998 | Caro et al. | ............ | 600/300 |
| 6,165,128 A * | 12/2000 | Cespedes et al. | ............ | 600/463 |
| 6,491,647 B1 * | 12/2002 | Bridger et al. | ............ | 600/585 |
| 7,125,383 B2 * | 10/2006 | Hoctor et al. | ............ | 600/438 |
| 7,318,804 B2 * | 1/2008 | Weitzel et al. | ............ | 600/438 |
| 2006/0247538 A1 * | 11/2006 | Davis | ............ | 600/481 |
| 2007/0016031 A1 * | 1/2007 | Mourad et al. | ............ | 600/437 |
| 2007/0049824 A1 * | 3/2007 | Konofagou et al. | ............ | 600/437 |
| 2008/0228086 A1 * | 9/2008 | Ilegbusi et al. | ............ | 600/479 |

* cited by examiner

*Primary Examiner* — Brian Casler
*Assistant Examiner* — Joel Lamprecht
(74) *Attorney, Agent, or Firm* — Harness, Dickey & Pierce, P.L.C.

(57) ABSTRACT

An optimized elastic modulus reconstruction procedure can estimate the nonlinear elastic properties of vascular wall from intramural strain and pulse wave velocity (PWV) measurements. A noninvasive free-hand ultrasound scanning procedure is used to apply external force, comparable to the force in measuring a subject's blood pressure, to achieve higher strains by equalizing the internal arterial baseline pressure. PWV is estimated at the same location where intramural strain is measured. The reconstructed elastic modulus is optimized and the arterial elastic modulus can be determined and monitored using a simple dual elastic modulus reconstruction procedure.

18 Claims, 20 Drawing Sheets

(a)　(b)

-1 mm　　　　　　　1 mm　　-50%　　　　　　　50%
(c)　(d)

(a)

(b)

-1 mm  1 mm (c)

-30%  30%

(d)

MEASUREMENT OF TISSUE ELASTIC MODULUS

CROSS-REFERENCE TO RELATED APPLICATIONS

This application claims priority to U.S. Provisional Application No. 60/849,073 filed on Oct. 3, 2006, which is incorporated by reference.

GOVERNMENT RIGHTS

Portions of the present disclosure were made with U.S. Government support under National Institutes of Health grant HL-68658. The U.S. Government has certain rights in the present disclosure.

All literature and similar materials cited in this disclosure, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this disclosure, including but not limited to defined terms, term usage, described techniques, or the like, this disclosure controls.

FIELD

The present disclosure relates to apparatus and methods using ultrasound pulse wave velocity and strain measurements for reconstructing the elastic modulus of tissue, such as arterial and vascular wall tissue.

INTRODUCTION

The statements in this section merely provide introduction information related to the present disclosure and may not constitute prior art.

Arterial compliance and elasticity are strong indicators of vascular disease, cardiovascular disease, peripheral vascular occlusive disease, diabetes, and renal failure. Changes in the collagen-to-elastin ratio in the extracelluar matrix of arterial media are believed to be one of the causes of arterial stiffness. Such changes are described by: Faury G, Function-structure relationship of elastic arteries in evolution: From microfibrils to elastin and elastic fibres, Pathol Biol 2001; 49:310-325; Bilato C, Crow M T, Atherosclerosis and vascular biology of aging, Aging (Milano) 1996; 8:221-234; and Bruel A, Oxlund H, Changes in biomechanical properties, composition of collagen and elastin, and advanced glycation endproducts of the rat arota in relation to age, Atherosclerosis 1996; 127:155-165.

In the early stage of atherosclerosis, fibrous lesions of several millimeters in diameter are scattered on the artery surface. As these lesions grow, the arterial wall homogeneously hardens toward the final stage of atherosclerosis. For early diagnosis, it is therefore important to measure the local hardness of the arterial wall.

By measuring mechanical properties of tissue, elasticity imaging using ultrasound can non-invasively monitor vascular pathologies developing within the vascular wall. Pressure equalization techniques can characterize nonlinear arterial elastic properties over a large deformational dynamic range, as described by Bank A J, Kaiser D R, Rajala S, Marchais S, Cheng A, "In Vivo human brachial artery elastic mechanics effects of smooth muscle relaxation", Circulation 100:41-47, 1999. A non-invasive free-hand ultrasound scanning procedure can be used to apply external force, comparable to the force generated in measuring a subject's blood pressure, in order to achieve higher strains by equalizing internal arterial baseline pressure. By lowering preload, it can be easier to differentiate diseased from normal arterial wall. Such methods are disclosed by Kim K, Weitzel W. F, Rubin J M, Xie H, Chen X, O'Donnell M, "Vascular Intramural Strain Imaging Using Arterial Pressure Equalization", Ultrasound in Med. & Biol. 30(6):761-771, 2004; and W F Weitzel, K Kim, J M Rubin, H Xie, and M O'Donnell, "Renal Advances in Ultrasound Elasticity Imaging: Measuring the Compliance of Arteries and Kidneys in End-Stage Renal Disease," Blood Purification, vol. 23, pp 10-17, (2005).

The precision of speckle tracking offers the possibility of detecting subtle underlying structural changes within the vascular wall and measuring corresponding intramural changes in elastic properties with unprecedented resolution, precision, and accuracy. Speckle tracking includes methods such as those disclosed in Lubinski M A, Emelianov S Y, O'Donnell M, "Speckle tracking methods for ultrasonic elasticity imaging using short time correlation", IEEE Transactions on Ultrasonics, Ferroelectrics, and Frequency Control 46:82-96, 1999. Methods and systems for measuring mechanical properties of vascular wall and for determining health of vascular structure are also described in U.S. Patent Application Publication 2005/0124892 to Weitzel et al.

Geometry models can be used to reconstruct the arterial elastic modulus. With some uncertainties, including arterial geometry factors and mechanical boundary conditions, the reconstruction procedure can differentiate a diseased artery from a healthy one. The inner radius of the artery can be determined from B-scan images and trashograms, but there can be more uncertainty in determining the outer boundary of the artery surrounded by the connective tissues. Geometrical uncertainties in elastic modulus reconstruction can be minimized using an independent measurement.

The elastic properties of the arterial wall help determine the propagation velocity of the pulse wave. Pulse wave velocity (PWV) measurement using an electrocardiogram (ECG) as a timing reference can be used, but it only reflects the average compliance over the extended arterial length, for example, between carotid and femoral, as reported by Asmar R, Benetos A, Topouchian J, Laurent P, Pannier B, Brisac A M, Target R, Levy B I, "Assessment of arterial distensibility by automatic pulse wave velocity measurement. Validation and clinical application studies," Hypertension, 26(3):485-90, 1995; and Millasseau S C, Stewart A D, Patel S J, Redwood S R, Chowienczyk P J, "Evaluation of Carotid-Femoral Pulse Wave Velocity. Influence of Timing Algorithm and Heart Rate," Hypertension 2005 Jan. 10. Doppler pulses can be recorded sequentially in two different arterial sites and compared using the R-wave of the ECG. The time delay over the estimated length between two measurement sites will determine the averaged PWV. However, in the early stage of atherosclerosis, fibrous lesions several millimeters in diameter are scattered on the artery surface. As these lesions grow, the arterial wall homogeneously hardens toward the final stage of atherosclerosis. For early diagnosis, it is therefore important to measure the local hardness of the arterial wall.

Tissue Doppler Imaging (TDI) can be used to acquire local PWV measurements as reported by Eriksson A, Greiff E, Loupas T, Persson M, Pesque P, Arterial pulse wave velocity with tissue Doppler imaging, Ultrasound in Med. & Biol. 2002; vol. 28: No. 5:571-580; and Persson M, Eriksson A, Persson W, Lindstrom K, "Estimation of Arterial pulse wave velocity with a new improved tissue Doppler method", Proceeding of the 23rd Annual EMBS International Conference: 188-191, 2001. However, tissue motion estimation from TDI has two major limitations for precise PWV measurements. First, TDI measurements are inherently Eulerian rather than Lagrangian, which means the same volume of tissue is not continually monitored over the cardiac cycle. A Lagrangian estimation of the displacement from velocity information using Doppler method is reported by Chubachi N, Kanai H, Murata R, and Koiwa Y, "Measurement of Local Pulse Wave Velocity in Arteriosclerosis by Ultrasonic Doppler Method", IEEE Ultrasonic Symposium 1747-1750, 1994, but the extrapolated displacement will not be as accurate as a directly estimated displacement. Second, to avoid aliasing artifacts, only very small tissue displacements can be monitored, producing low signal-to-noise (SNR) measurements of motion.

Consequently, there is a need for improvements in measuring arterial compliance independent of geometry and mechanical boundary conditions. Apparatus and methods that reconstruct the elastic modulus of arterial and vascular wall tissue would enhance measurement and quantitation of arterial compliance. Such apparatus and methods would provide significant advantages in diagnosing and monitoring vascular disease, cardiovascular disease, peripheral vascular occlusive disease, diabetes, and renal failure.

SUMMARY

In some embodiments, the present disclosure provides methods of monitoring vascular wall compliance comprising measuring intramural strain; measuring pulse wave velocity; and reconstructing an elastic modulus for the vascular wall using the intramural strain and pulse wave velocity.

In some embodiments, the present teachings provide a system for determining the vascular health of a patient comprising means for measuring intramural strain of a vascular wall; means for measuring pulse wave velocity of a vascular wall; means for reconstructing an elastic modulus of the vascular wall using the intramural strain and pulse wave velocity measurements; and means for comparing the elastic modulus to the elastic modulus of diseased and healthy vascular wall.

The present disclosure affords various benefits which include using pulse wave velocity (PWV) estimation based on speckle tracking to overcome two shortcomings of tissue motion estimation using tissue Doppler imaging (TDI). Namely, the apparatus and methods of the present disclosure allow the same volume of tissue to be continually monitored over the cardiac cycle while also avoiding aliasing artifacts.

The present disclosure uses an ultrasound probe to scan a small segment of an artery along the axis of wave propagation. Speckle tracking estimates the time delay between ultrasound beams and the PWV can be determined from the time delay across the known distance between the ultrasound beams.

The methods and apparatus described herein can be used to reconstruct the elastic modulus of tissue (e.g., arterial and vascular wall). Reconstruction of the elastic modulus allows quantitation of arterial compliance independent of geometry and mechanical boundary conditions. Both elastic modulus reconstructions from intramural strain and PWV measurements can be corrupted due to their dependency on arterial geometry. The present teachings combine these two measurements thereby removing most of this uncertainty and enabling elastic modulus reconstruction.

Thus, the teachings of the present disclosure provide dual ultrasound imaging techniques with pressure equalization that enable accurate assessment of peripheral vessel compliance, including noninvasive measurements of arterial and vascular wall tissue, for example such as the carotid artery.

DRAWINGS

The drawings described herein are for illustration purposes only and are not intended to limit the scope of the present teachings in any way.

Figure 4:
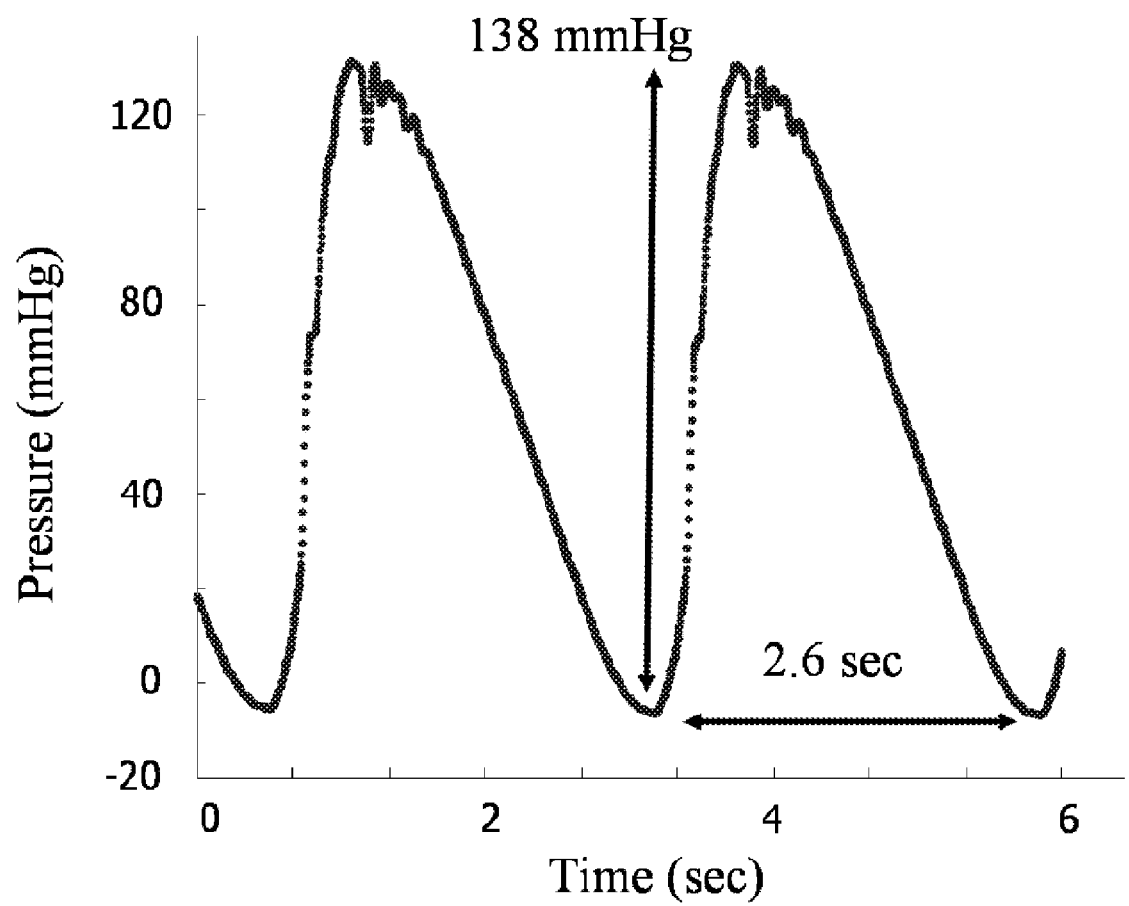
Figure 5:
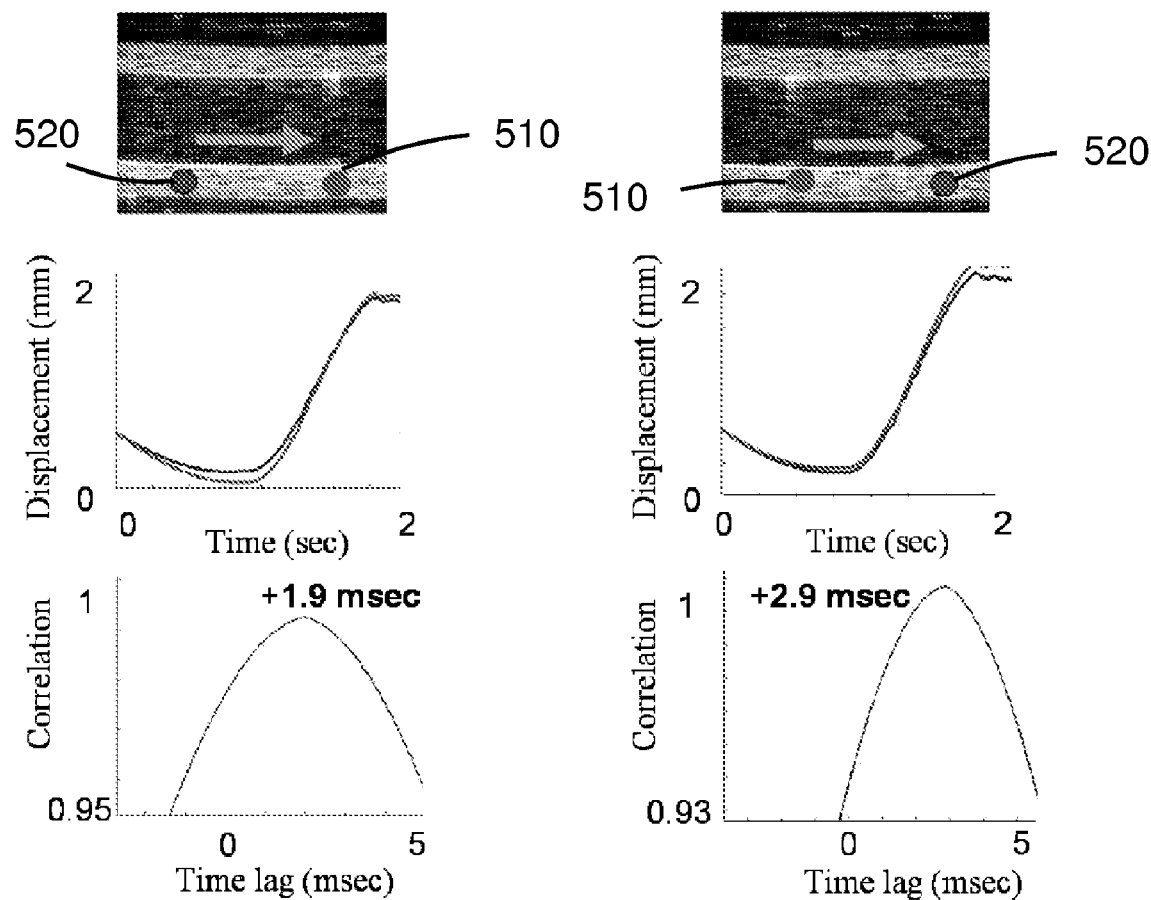
Figure 6:
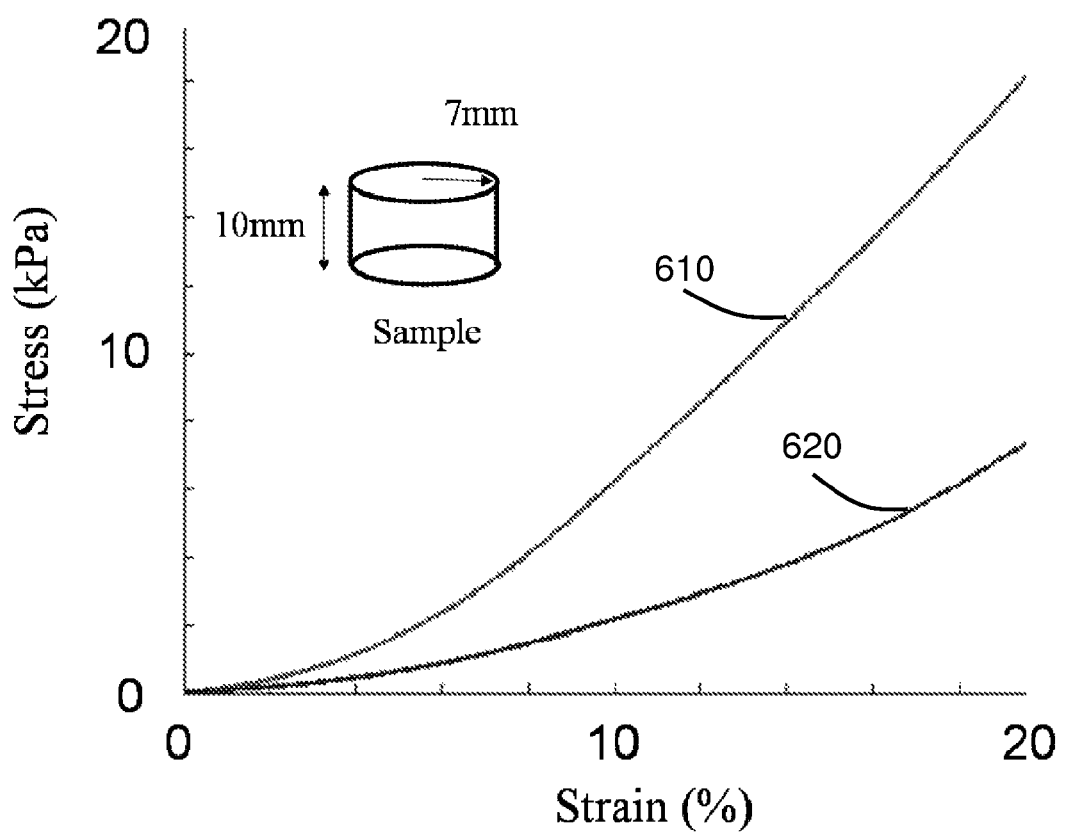
Figure 7:
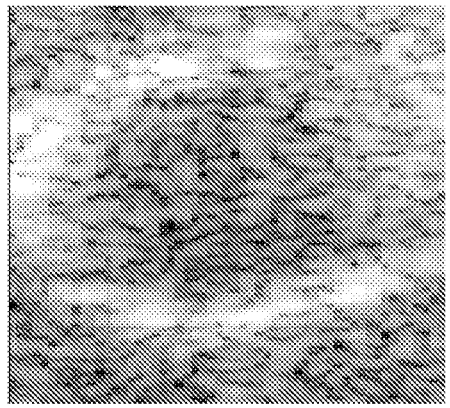
Figure 7:
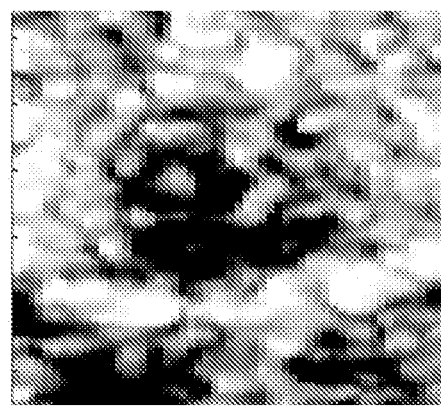
Figure 7:
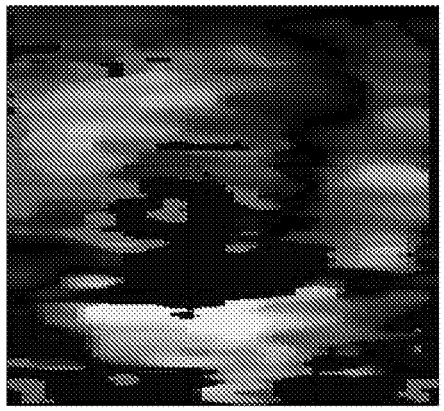
Figure 7:
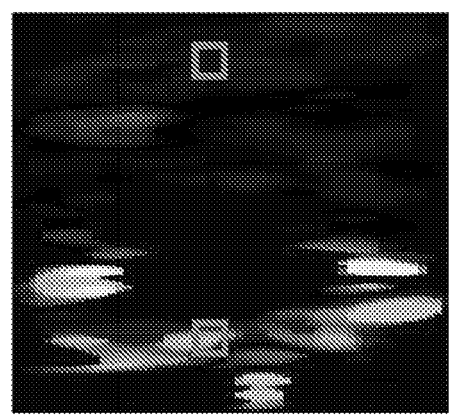
Figure 8:
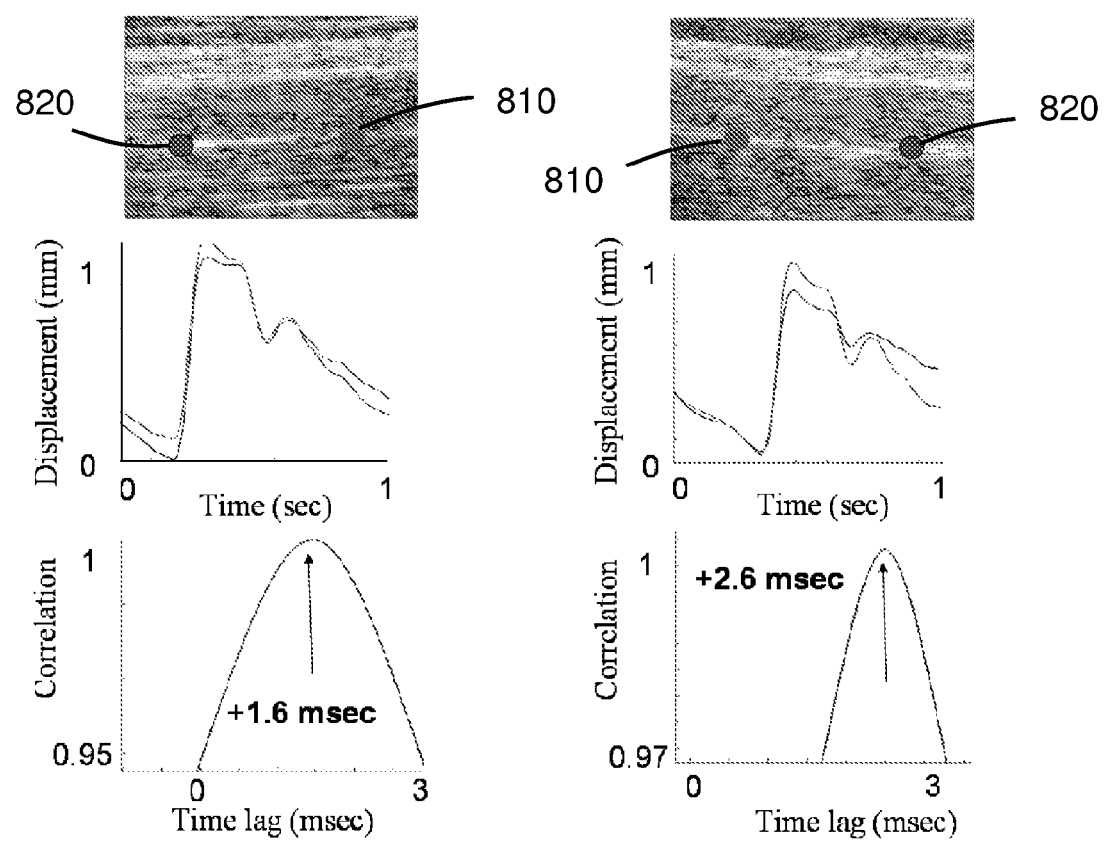
Figure 9:
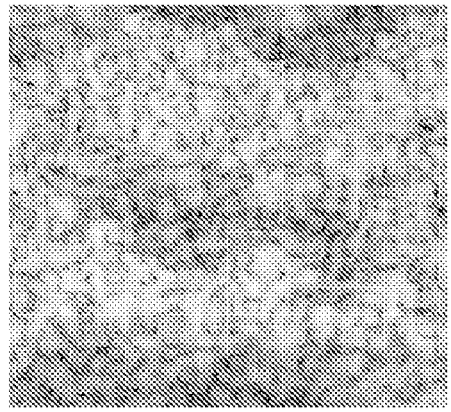
Figure 9:
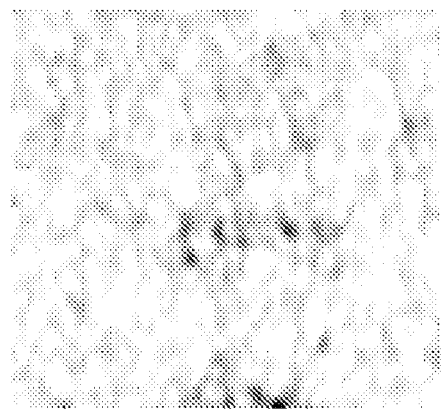
Figure 9:
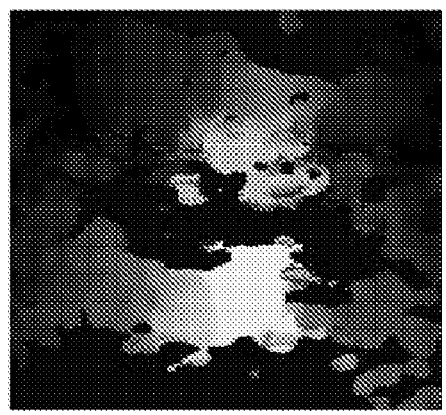
Figure 10:
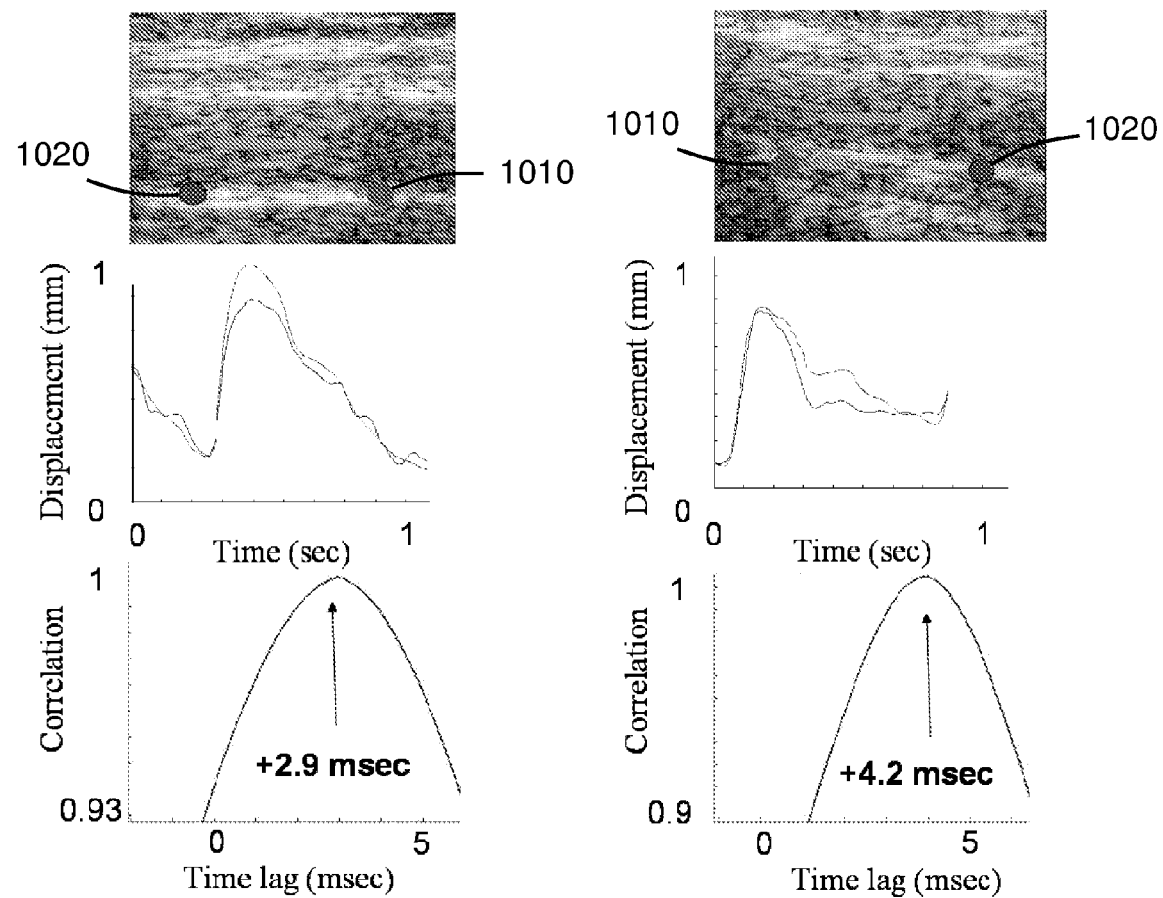
Figure 11:
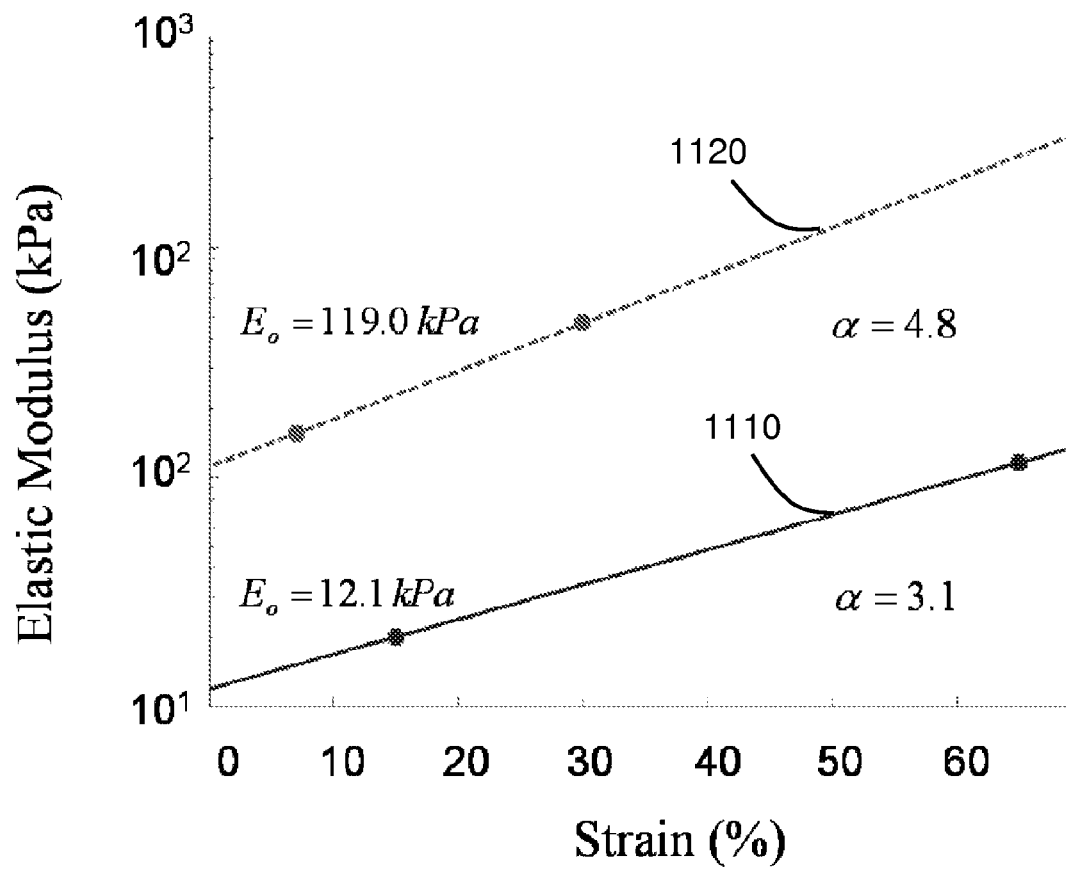
Figure 12:
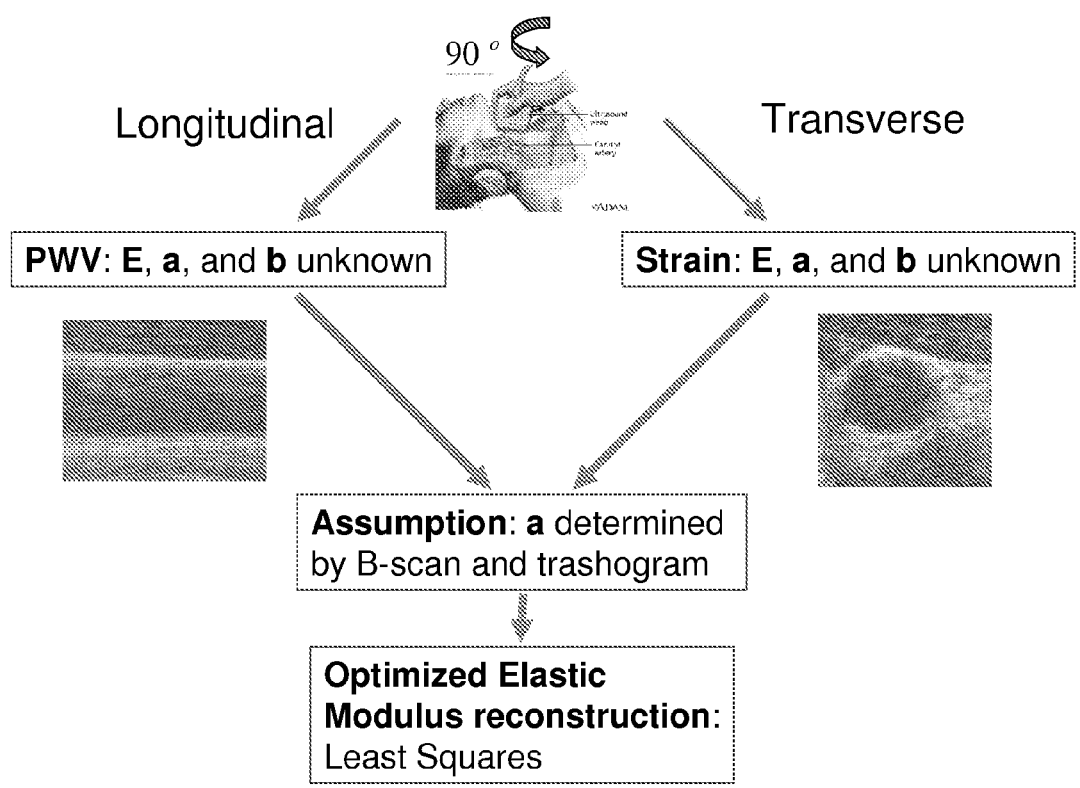
Figure 13:
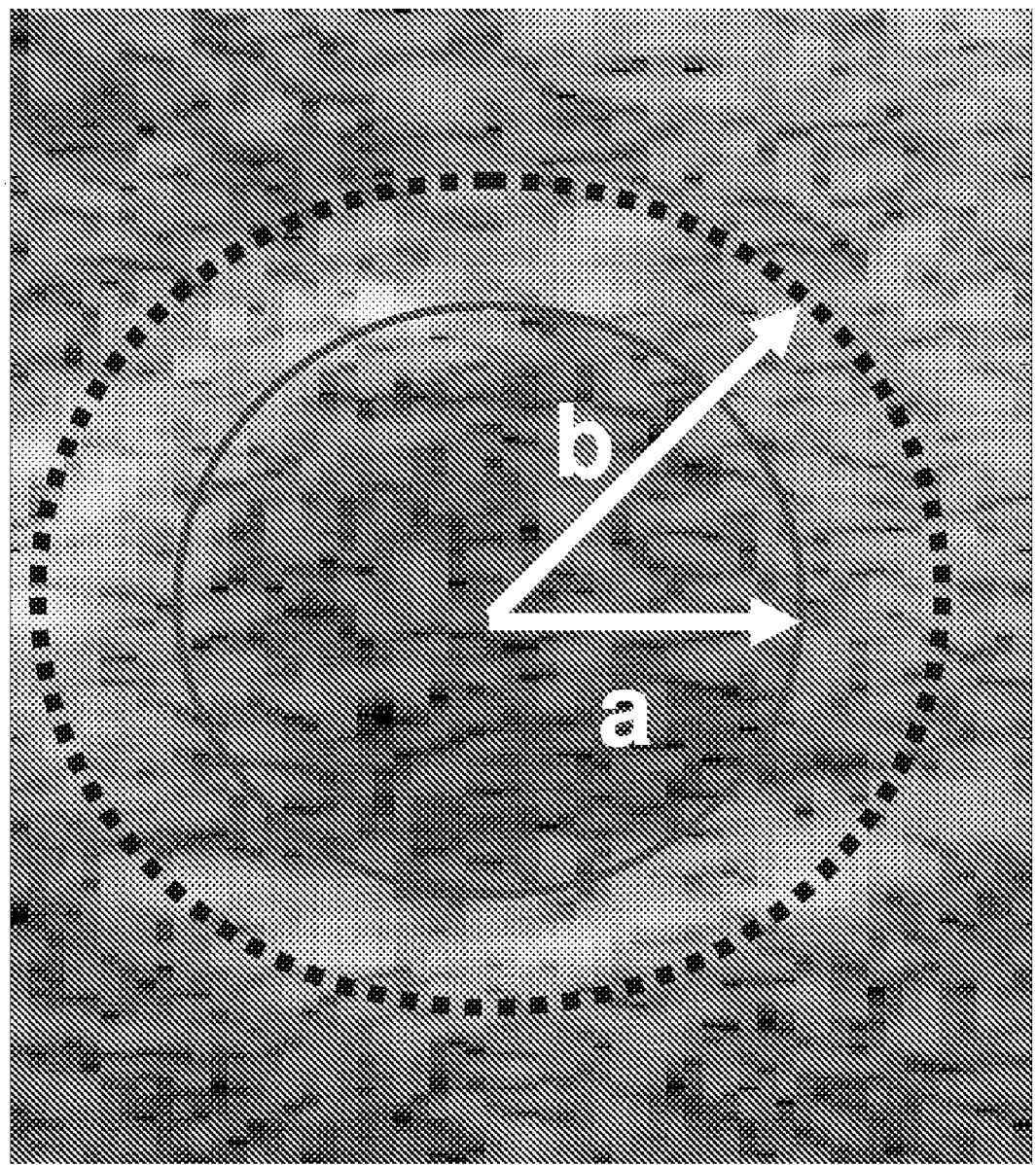
Figure 14:
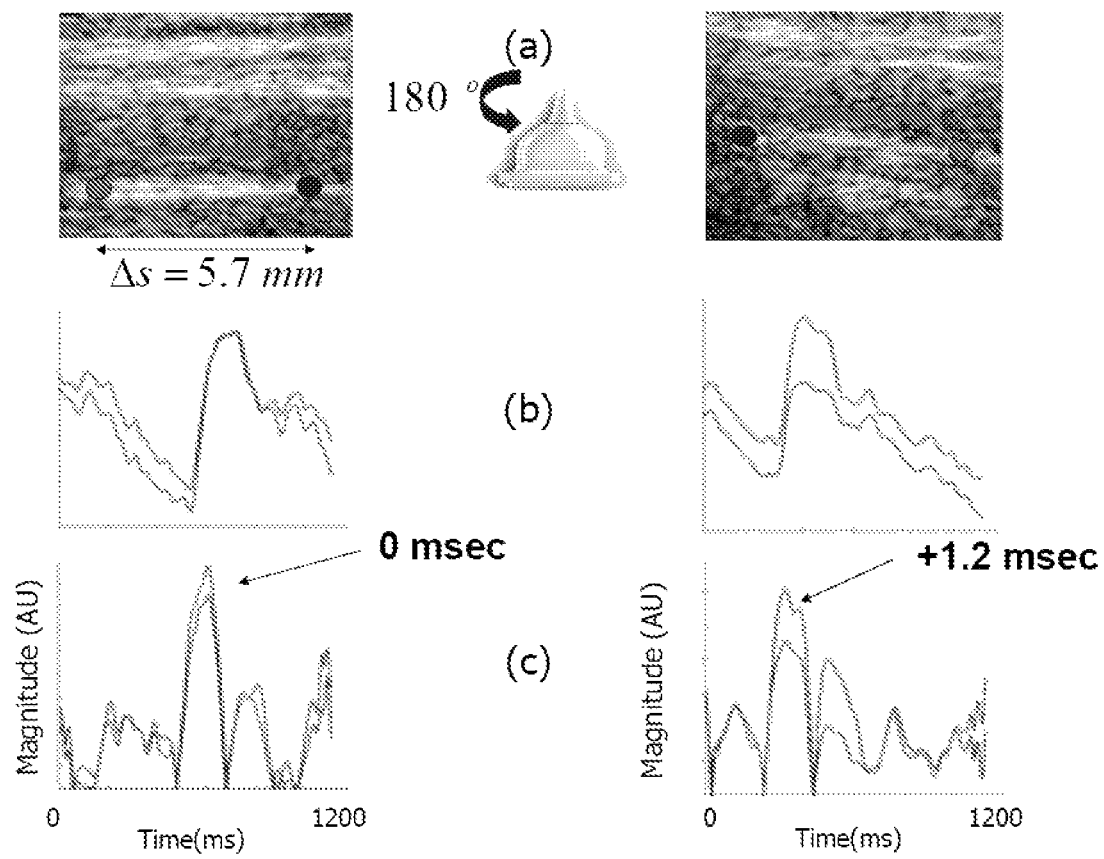
Figure 15:
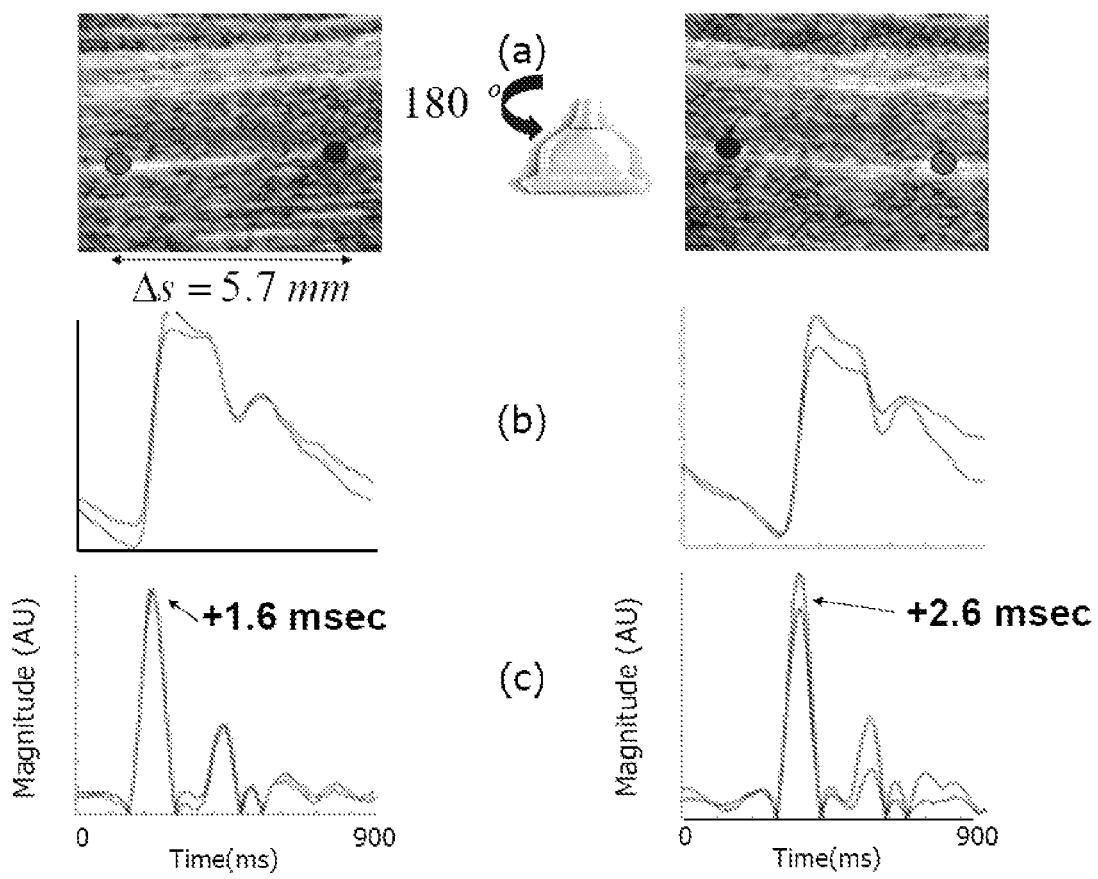
Figure 16:
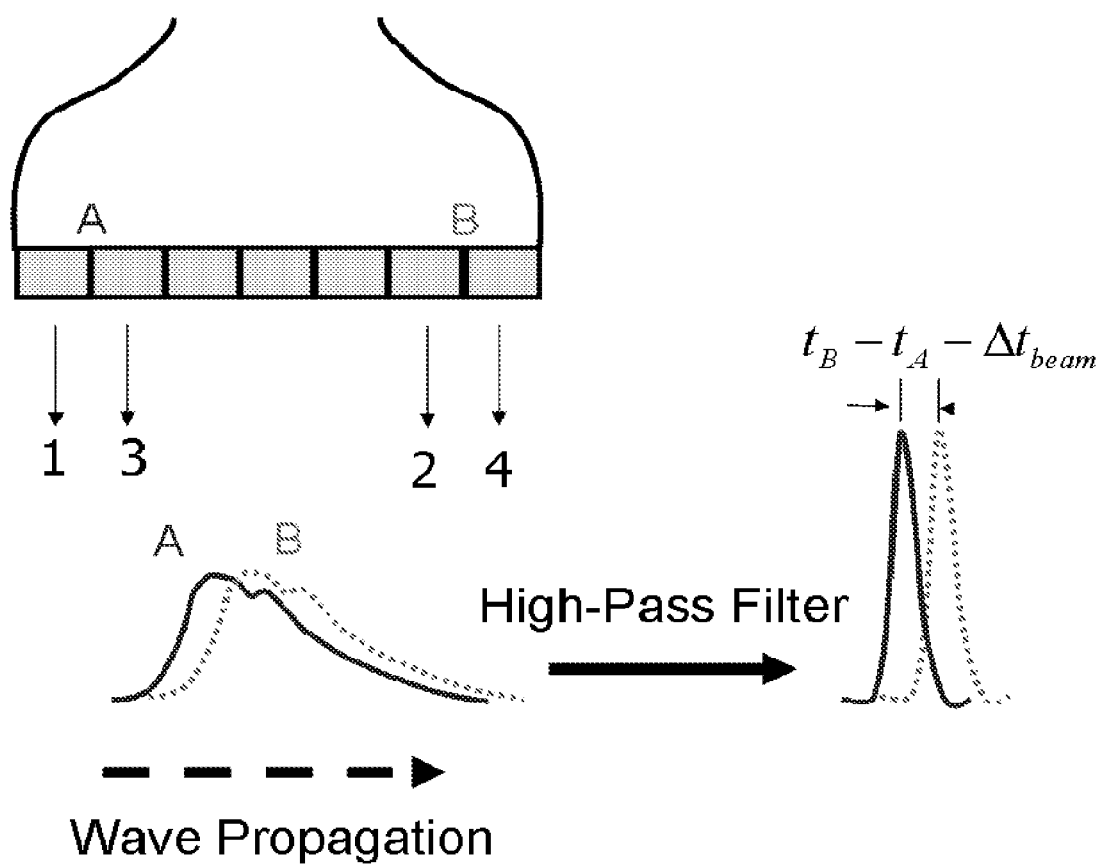
Figure 17:
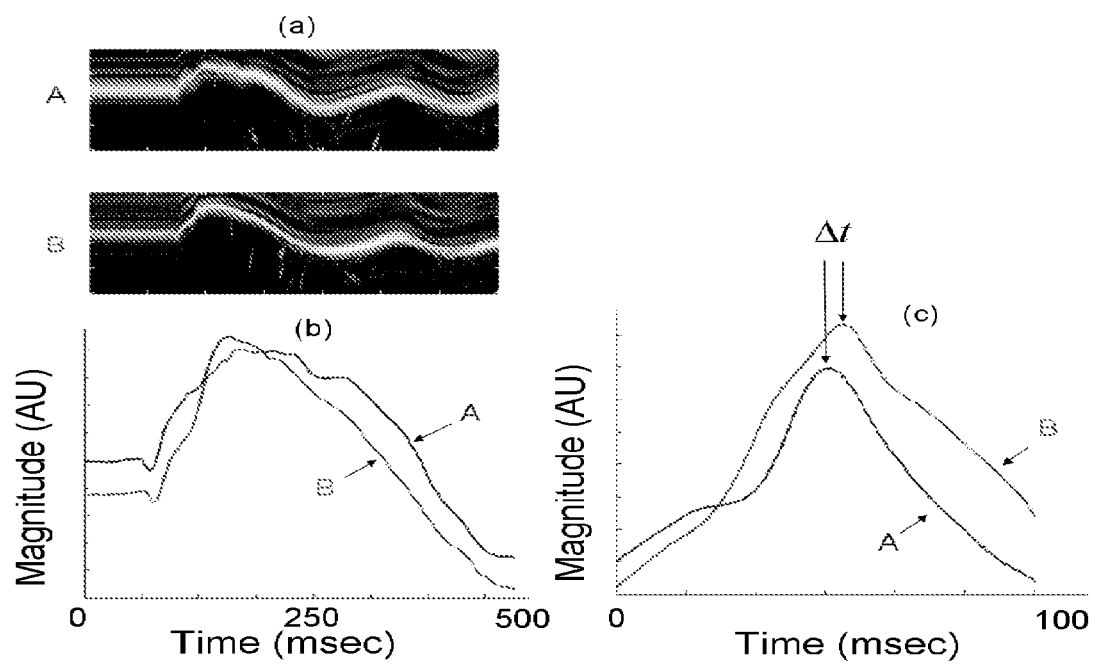
Figure 18:
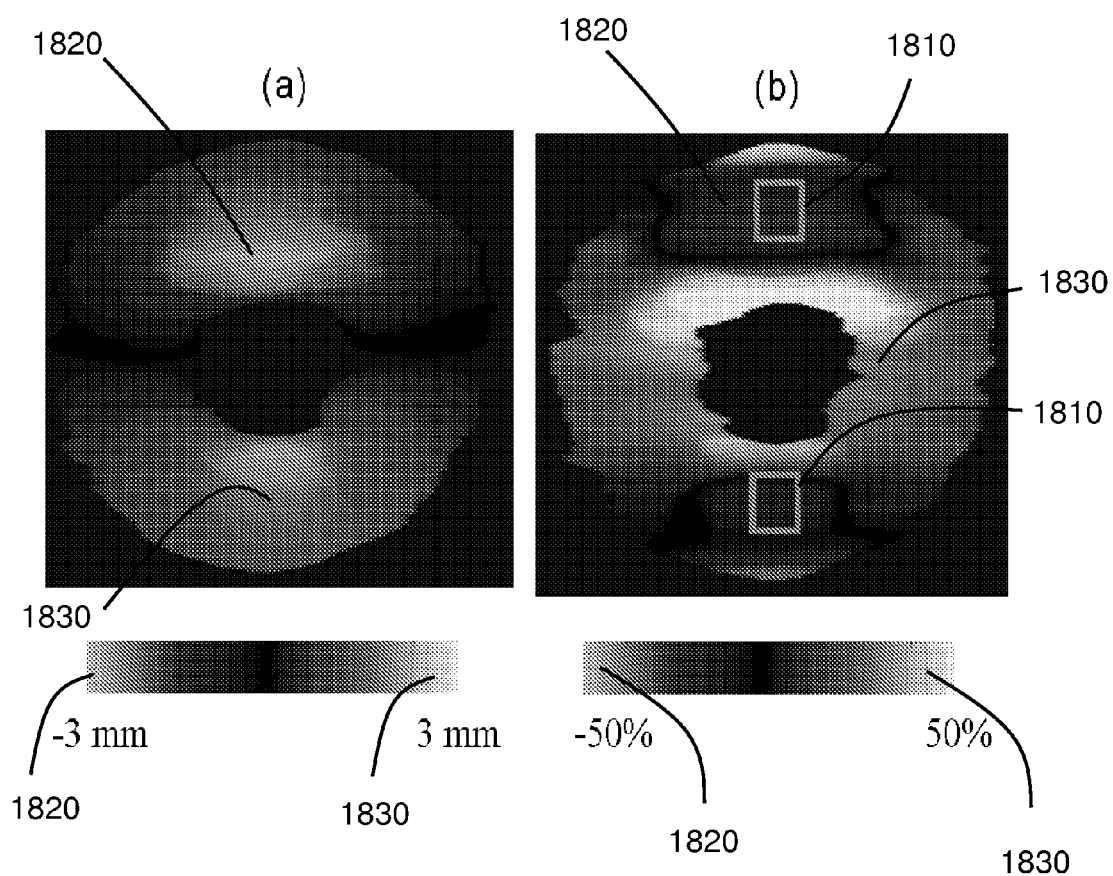
Figure 19:
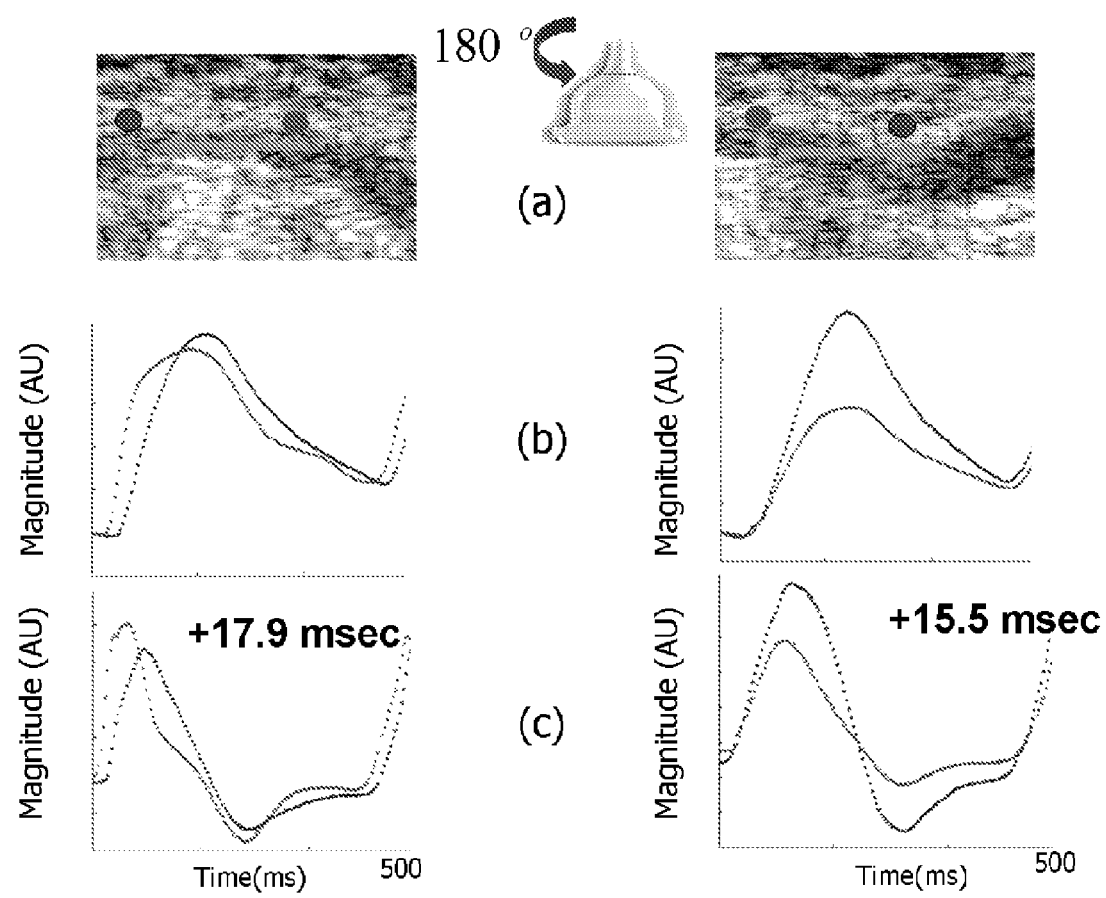

FIG. 4 graphically depicts pulse pressure measurement for the rubber phantom;

FIG. 5 illustrates measurement of the PWV for the rubber phantom in a longitudinal scan;

FIG. 6 graphically depicts the stress-strain curve of direct mechanical measurements;

FIG. 7 shows the intramural strain measurement of the healthy subject after pressure equalization using a transverse scan;

FIG. 8 graphically depicts the PWV for the healthy subject after pressure equalization using a longitudinal scan;

FIG. 9 shows the intramural strain measurement of the healthy subject after pressure equalization using a transverse scan;

FIG. 10 shows the PWV for the healthy subject after pressure equalization: Longitudinal scan;

FIG. 11 shows the arterial elastic modulus reconstruction over a large deformational dynamic range;

FIG. 12 is a schematic of optimized elastic modulus reconstruction using a least squares method with intramural strain and PWV measurements obtained from transverse and longitudinal scans of an artery;

FIG. 13 illustrates an ultrasound image of a brachial artery cross section;

FIG. 14 illustrates PWV measurement under physiological pressure;

FIG. 15 illustrates PWV measurement after pressure equalization;

FIG. 16 illustrates near parallel mode for PWV;

FIG. 17 illustrates PWV measurement on a rubber phantom;

FIG. 18 illustrates transverse scanning for strain measurement;

FIG. 19 illustrates PWV measurement after pressure equalization; and

Figure 20:
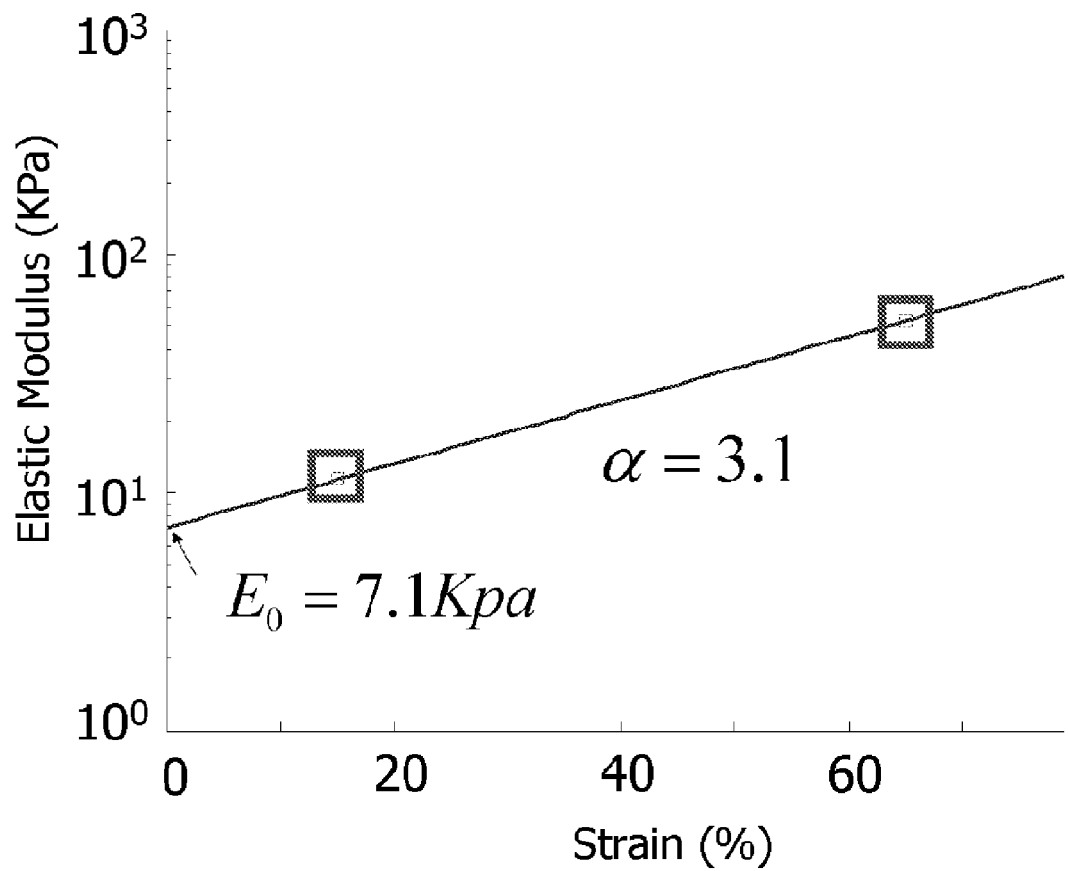

FIG. 20 illustrates elastic modulus reconstruction over full dynamic range.

DETAILED DESCRIPTION

Further areas of applicability will become apparent from the description provided herein. It should be understood that the description and specific examples are intended for purposes of illustration only and are not intended to limit the scope of the present disclosure.

The present disclosure provides methods and apparatus for optimized elastic modulus reconstruction procedures to determine local nonlinear elastic properties of tissue. In some embodiments, methods and apparatus of the present disclosure can be used to determine the elastic properties of arterial and vascular wall tissue. Elastic properties, including elastic modulus, of vascular wall can be determined using measurements including intramural strain and pulse wave velocity (PWV).

In some embodiments, elasticity changes due to a local lesion can be accurately determined by a transverse scan for intramural strain measurement. However, a small lesion can be missed if the imaging protocol does not scan densely enough along the extended region of the artery. Longitudinal scanning for local PWV measurement with an ultrasound probe can span several centimeters. The PWV estimated from the time delay between two ultrasound beams at each end of the ultrasound probe reflects the average elastic property of the artery over the scan region. Using different beam combinations, PWV can be estimated at multiple points along the length of the longitudinal scan. The location of the lesion can be determined by comparing the PWV at proximal and distal ends.

In combination with pressure equalization techniques, transverse strain measurements can differentiate a healthy subject's tissue from a diseased subject's tissue. To quantitatively characterize arterial elasticity, elastic modulus reconstruction is necessary. Reconstruction from either PWV or intramural strain measurement involves geometrical uncertainty, including inner and outer radii of the artery. To minimize the effects of these uncertainties and variable mechanical boundary conditions, the present teachings provide optimized reconstruction procedures that combine intramural strain and PWV.

In some embodiments, intramural strain with pressure equalization can be used to separate a healthy subject from a diseased one. A linear least squares fit to the natural log of the estimated elastic modulus as a function of preload can be used to characterize nonlinear arterial mechanical properties. Elastic properties of the surrounding tissue can influence the fit, but should not significantly alter the results except in the small preload limit of highly compliant arteries. Both the intercept (i.e., the elastic modulus of the undistended artery) and the nonlinear parameter (i.e., the slope of the fit) can be used to assess arterial compliance. If the elastic modulus of surrounding material is considered small compared to the vessel elastic modulus, the intercept $E_o$ will determine the undistended (i.e., zero preload) in-vivo vessel elastic modulus. Otherwise, the elastic modulus of surrounding tissue can be measured to correctly reconstruct the vessel elastic modulus. Similarly, if the ratio of elastic moduli between the wall and surrounding muscle remains high over preload, then the slope of this curve (i.e., the nonlinear coefficient) can be correctly reconstructed independent of the elastic modulus of the surrounding tissue. Since surrounding tissue modulus may be comparable between subjects, overestimation for the diseased subject can be much less pronounced than that for normal subjects. In addition, the nonlinear coefficient can be significantly larger for the diseased subject.

EXAMPLES

Example A

Ex-Vivo Phantom Model

An elastic modulus reconstruction procedure can be developed from independent measurements of intramural strain and PWV. A rubber phantom model is used to demonstrate the present teachings.

PWV Estimation Using Near Parallel M-Mode: Longitudinal Scan

Time delay over the estimated local distance between two measurement sites determines local PWV. To avoid any interference from reflections, the first arrival part of the wave can be chosen to estimate the time delay. However, as the wave initiates, the signal is not high enough to correctly estimate the time delay. To overcome this, the sharp edge corresponding the start of systole can be high-pass filtered to accurately estimate time delay (temporal resolution) before the reflected part of the wave interferes (i.e., by causality, a significant reflection cannot proceed the primary signal).

Correlation-based phase sensitive speckle tracking can be used to trace the frame-to-frame intramural wall displacement on each ultrasound beam. Speckle tracking can include methods as disclosed in Lubinski M A, Emelianov S Y, O'Donnell M, "Speckle tracking methods for ultrasonic elasticity imaging using short time correlation", IEEE Transactions on Ultrasonics, Ferroelectrics, and Frequency Control 46:82-96, 1999. Frame-to-frame displacement estimates can be integrated from and registered to the initial coordinate system (i.e., Lagrangian presentation).

Figure 1:
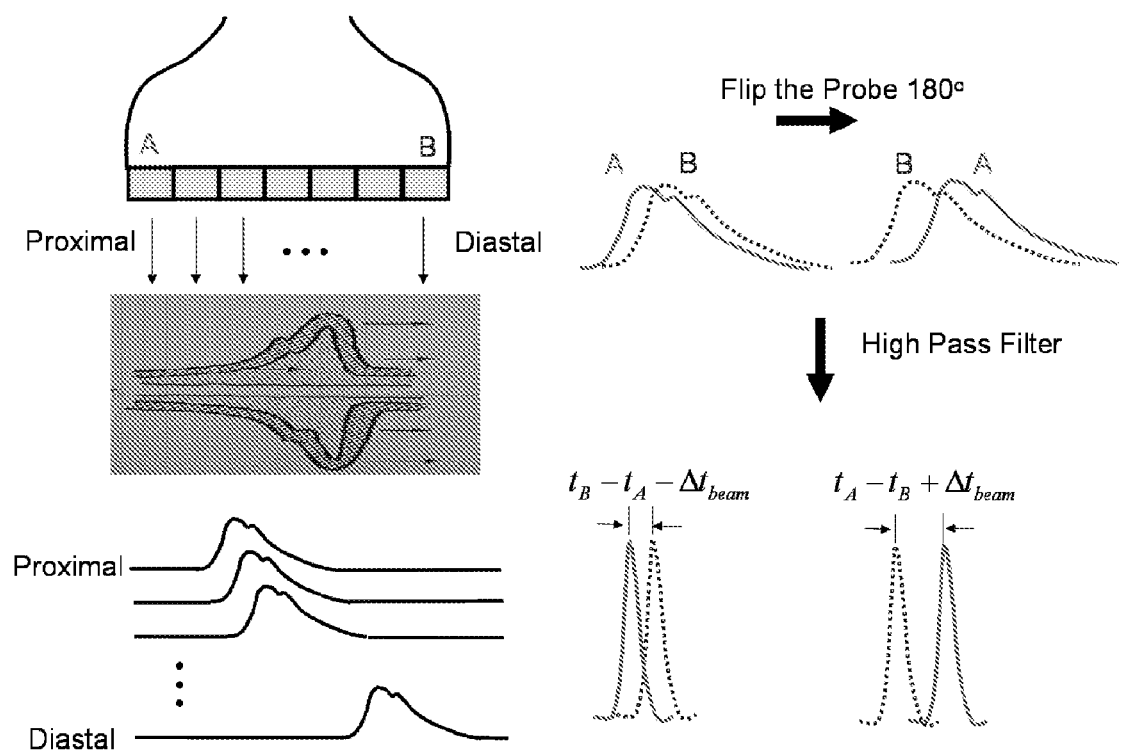
FIG. 1 illustrates pulsed wave velocity (PWV) measurement using near parallel M-mode.

FIG. 1 illustrates PWV measurement using near parallel M-mode. The registered displacement referenced to the original frame reconstructs the entire sequence of pulse wave (bottom left of FIG. 1) at each ultrasound beam. Time derivative of the signal produces a high peak at the onset of the systole (bottom right in FIG. 1). To estimate the time delay between two measurement sites along the ultrasound probe, the derivatives of the two signals were cross-correlated. The peak of the correlation coefficient determines the time delay. The ultrasound probe is reversed for the second measurement at the same spot. Averaging of the two measurements will cancel the time delay introduced by the pulse sequence and produces the time delay due to pulse wave propagation.

The registered displacement reconstructs the entire sequence of the pulse wave, as shown in the left panel of FIG. 1. To increase the time resolution maintaining the original wave form, an interpolation can be performed as needed. Time derivative of the signal produces a high peak at the onset of the systole (right panel in FIG. 1). To estimate the time delay between two measurement sites along the ultrasound probe, the derivatives of the two signals can be cross-correlated. The peak of the correlation coefficient determines the time delay. This time delay includes the time delay introduced by the pulse/receiving sequences. To eliminate this, the time delay was measured one more time with the ultrasound probe reversed. The difference in time delay between these two measurements results in the physical delay due to propagation of the pressure pulse, as illustrated in FIG. 1.

A high frame rate is needed to measure the time delay, typically on the order of milliseconds over the length of an ultrasound probe, extending several tens of millimeters. A specially designed RF collection system with near parallel M-mode employing an ultra high frame rate (up to 500 Hz) with lowered ultrasound beam number (32 beams) is installed on a commercial ultrasound scanner (iU22, Philips, Seattle, Wash.). A 12 MHz linear array (L12-5, Philips) is used. RF data from every frame in the sequence is captured at a rate of 381 frames per second for 10 seconds.

Figure 2:
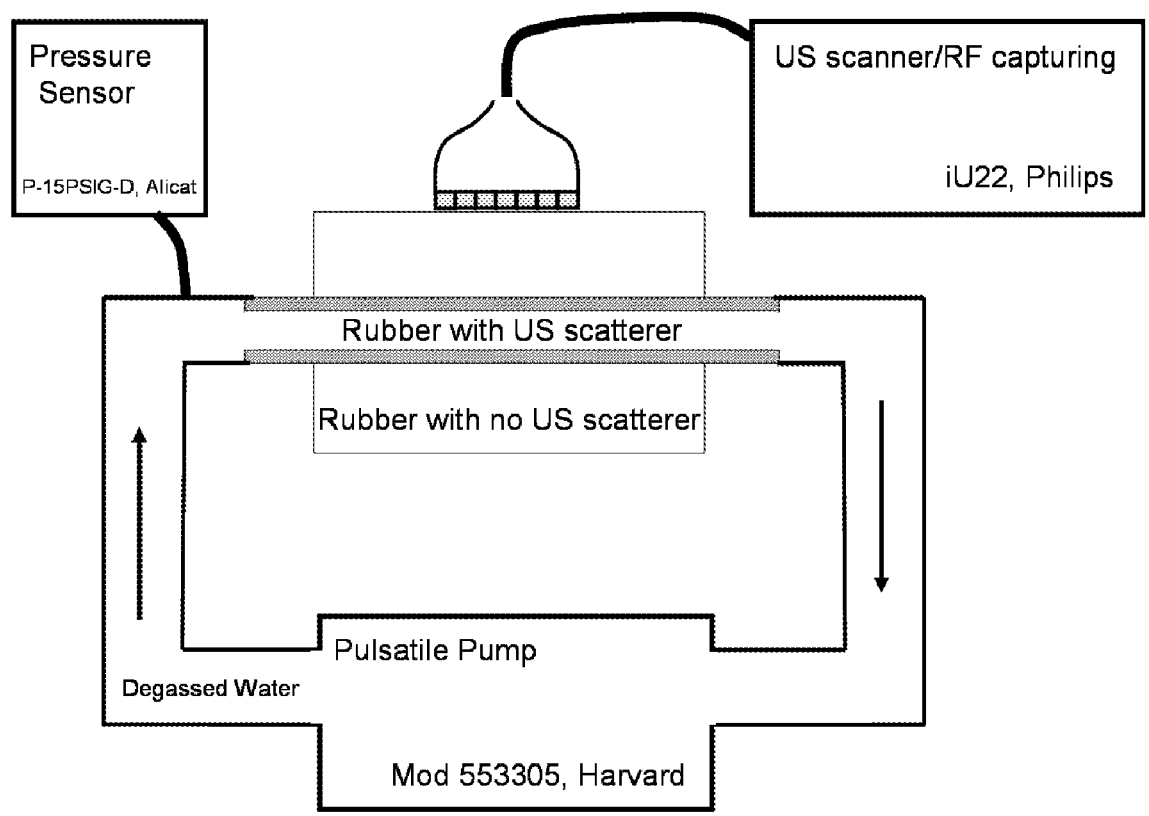
FIG. 2 is a schematic illustration of an exemplary apparatus constructed in accordance with the teachings of the present disclosure.

A cylindrical rubber phantom seeded with 0.4% by weight polystyrene spheres (Amberlite, Sigma Chemical Co., MO) is used. The phantom is over 300 mm long, 15.9 mm in diameter, and had an inner lumen 9.2 mm in diameter. To avoid any undesired translational motion, the artery phantom was embedded in a soft rubber phantom block; there were no ultrasound scatterers in this block. It was soft and large enough to minimize any boundary effects (over 100 mm by 100 mm by 300 mm). The artery phantom was connected to a pulsatile pump (Model 553305, Harvard Apparatus, Holliston, Mass.) acting as the pulse pressure source (FIG. 2.). Internal cyclic pressure was monitored and recorded using a pressure sensor (P-15PSIG-D/5P, Alicat Scientific Inc., Tucson, Ariz.), connected into lumen about 30 mm away from the ultrasound measurement site.

Intramural Strain Estimation: Transverse Scan

While the arterial phantom undergoes cyclic deformation, the same linear ultrasound array (L12-5, Philips) used for PWV measurement imaged the cross section along the short axis of the phantom at a rate of 101 frames per second for 10 seconds, as shown in FIG. 2.

FIG. 2 depicts the ex-vivo experimental set-up using a rubber phantom. The pulsatile pump generates pulse pressure through the rubber phantom. The lumen pressure was recorded while ultrasound RF data were captured with a commercial ultrasound scanner.

RF data from every frame in the sequence were captured. The intraluminal pressure over time was also recorded. Data were subsequently processed using phase-sensitive, two-dimensional speckle-tracking to determine intramural displacements and strains. Frame-to-frame lateral and axial displacements were estimated from the position of the maximum correlation coefficient, where the correlation kernel size equaled the speckle spot for optimal strain estimation and axial displacements were refined using the phase zero-crossing of the complex correlation function. Frame-to-frame displacement estimates were integrated from and registered to the initial coordinate system (i.e., Lagrangian presentation). Spatial derivatives of the displacements were computed in one region of the artery to estimate the radial normal strain (i.e., the radial derivative of the radial displacement). The radial normal strain is also referred to herein as strain. The recorded pulse pressure was used for elastic modulus reconstruction.

Optimized Elastic Modulus Reconstruction

A simple model, assuming incompressibility, plane strain in the cross-section of the artery phantom, and small effects by soft surrounding material, relates elastic modulus E of the artery wall to pulse pressure ($\Delta p$) and inter-cardiac strain ($\Delta \epsilon$) by $$E = K\left[\frac{\Delta p}{\Delta \varepsilon}\right], \quad (1)$$

where $$K = \frac{-3a^2 b^2}{2(b^2 - a^2)r^2},$$

a is the lumen radius, b is outer radius of the artery, and r is the strain measurement point, as further described by Kim K, Weitzel W. F, Rubin J. M., Xie H., Chen X, O'Donnell M., "Vascular Intramural Strain Imaging Using Arterial Pressure Equalization", Ultrasound in Med. & Biol. 30(6):761-771, 2004. The pulse pressure generated by inter-cardiac blood volume change over the cardiac cycle propagates through the arterial wall. The elastic property of the arterial wall plays an important part in determining the propagation velocity of the pulse wave, as shown in Eq. (2):

$$PWV = \sqrt{\frac{hE}{2a\rho(1-v^2)}} = \sqrt{\frac{2hE}{3a\rho}}, \quad (2)$$

where $\rho$ is density, a is radius, h is thickness, E is elastic modulus and v is Poisson's ratio of the artery, assumed to be ½ for an incompressible medium. Eq. (2), originally derived in Bergel D H, "The dynamic elastic properties of the arterial wall," J. Physiol. 156:458-469, 1961, represents a modified Moens-Korteweg equation properly accounting for wall thickness.

In both cases, artery geometrical factors, including inner and outer radius, can be determined. Arterial inner radius, a, can be measured from B-scan and correlation maps at relatively high accuracy. Combining these two equations leads to the equation for the ratio of outer radius to inner radius (b/a):

$$\left(\frac{\Delta p}{\Delta \varepsilon}\right) \frac{\left(\frac{b}{a}\right)^2}{\left[\left(\frac{b}{a}\right)+1\right]^3} = \left(\frac{\rho}{4}\right) PWV^2. \quad (3)$$

Out of three possible solutions for (b/a), only one positive and real solution greater than unity is taken. In the case where there is more than one real solution greater than unity, the smallest value should be taken to satisfy the assumption that the wall is sufficiently thin so that the inertia can be neglected in comparison with that of fluid, as described in King A L, "Waves in elastic tube: Velocity of the pulse wave in large arteries," J. Applied Physics Vol. 18, 595-600, 1947. For the ex-vivo experiment, the density, $\rho$, was measured and for the in-vivo scan, the nominal value for arterial tissue (1071-1100 kg/m^3) was used. Once b is obtained, the elastic modulus can be determined either from Eq. (1) or Eq. (2).

Direct Mechanical Measurement

A mechanical system capable of measuring the elastic modulus of small tissue samples was used, as described in Erkamp R Q, Wiggins P, Skovoroda A R, Emelianov S Y, O'Donnell M, "Measuring the Elastic Modulus of Small Tissue Samples," Ultrasonic Imaging 20:17-28, 19. This system tolerates the constraints of biological tissue, such as limited sample size ($\leq 1.5$ cm$^3$) and imperfections in sample geometry. The conversion factor to transform the slope of a stress-strain curve to a Young's modulus, obtained from finite element analysis was also used. The same rubber phantom used for ultrasound strain and PWV measurements was cut into a small cylindrical piece to fit into the sample holder. The strain and the resulting force under conditions of continuous deformation of the sample were simultaneously measured and used to determine the elastic modulus.

Ex-Vivo Phantom Measurements

Wall displacement was estimated using 0.2 mm×0.4 mm (axial×lateral) correlation kernel. Frame-to-frame displacements were accumulated from diastole to systole. The spatial derivative of the accumulated displacement in the direction of ultrasound beam determines the intramural normal strain. The average intramural inter-cardiac strain was about 19%.

Figure 3:
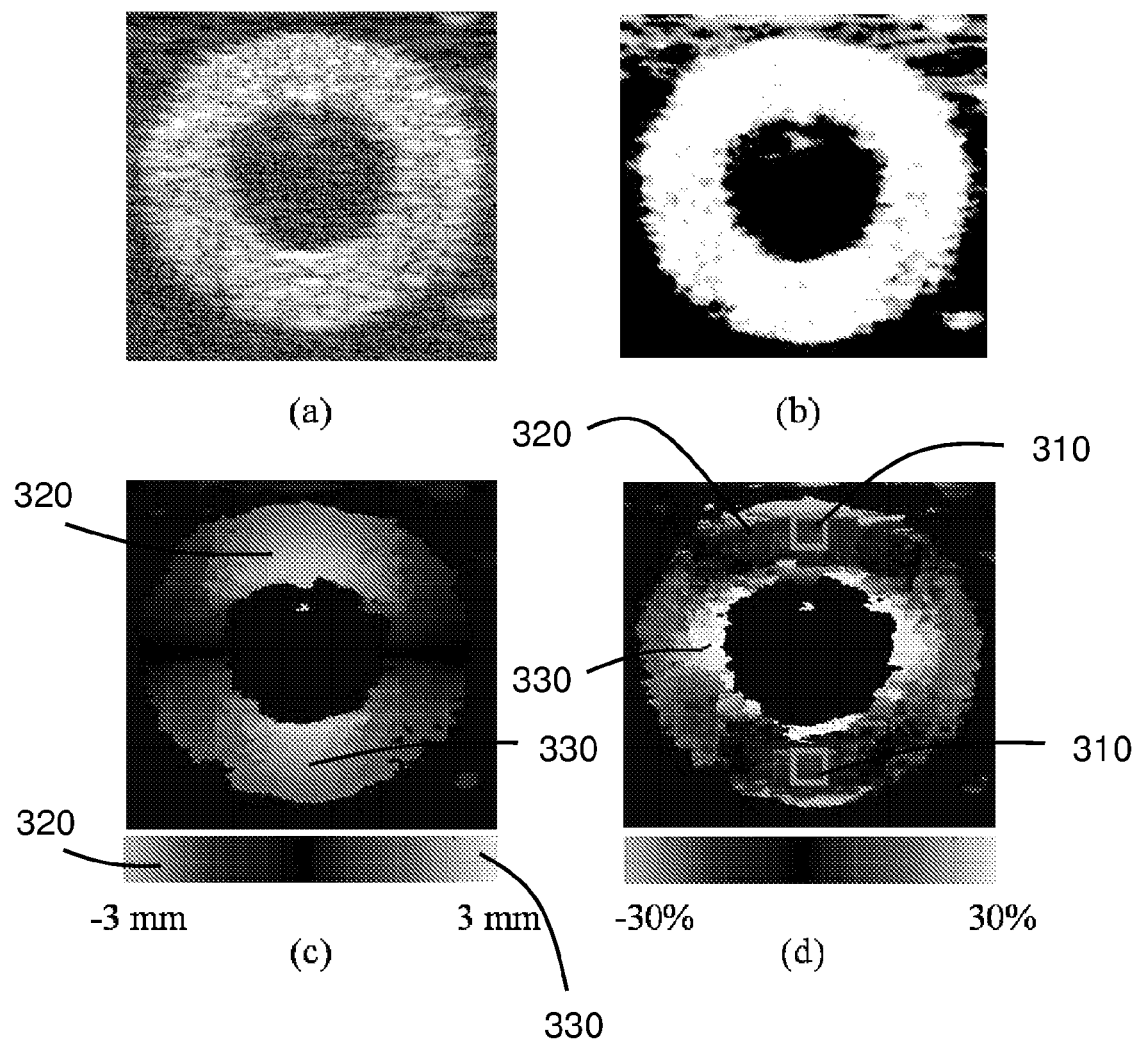
FIG. 3 depicts the intramural strain measurement of the rubber phantom transverse scan.

FIG. 3 depicts the intramural strain measurement of the rubber phantom: Transverse scan. (a) is the B-scan image; (b) correlation coefficient map; (c) accumulated axial displacement from diastole to systole; (d) axial normal strain measurement, the spatial derivative of (c). Note that the transducer is at the top of each image. The average strain on the top and bottom wall over the extended regions marked as boxes 310 in panel (d) was about 19%.

The correlation coefficient ranges from 0.9 to 1 in FIG. 3(b), and the axial displacement is presented over a −2 mm to +2 mm range in FIG. 3(c). Blue color 320 represents motion toward the transducer and red color 330 represents motion away from the transducer for this display. Note the transducer is at the top of each panel. The bottom right panel is a strain map ranging from −30% to 30%. The side walls expand nearly as much as the top and bottom contract, demonstrating near incompressibility of the rubber phantom. The strain was averaged over the extended region of the top and bottom wall as marked in the figure. Artifacts around inside and outside boundaries were ignored.

The pulse pressure was measured to be 138 mmHg, as shown in FIG. 4. The pressure was taken near the rubber phantom. The small fluctuation might come from unstable dynamic system response. This does not affect the estimated pulse pressure. The pulsatile pump was set with 15 cc/stroke, 20 rpm, and 25/75 for systole/diastole ratio. A small fluctuation occurred right after peak pressure. This fluctuation might be from instable flow response of the closed loop system and should not affect the magnitude of the pulse pressure. The inner and outer radius of artery phantom, a and b, were determined to be 4.62 mm and 7.95 mm respectively both from B-scan (a) and trashogram (b) depicted in FIG. 3.

At the same measurement site, the transducer was simply rotated by 90 degrees to measure PWV. The beam number was lowered to 32 with a frame rate of 381 Hz. Phase-sensitive correlation based speckle tracking was employed only in the axial direction to trace intramural displacement along the beam direction. The sharp edge at the onset of systole was high pass filtered to accurately determine the time delay between two measurement sites. The correlation between filtered signals resulted in a time delay of 1.9 ms when the probe is positioned along the wave propagation. The time delay when the probe rotated 180° was 2.9 ms. The average time delay of 2.4 ms due to the pulse wave traveling time between two beams separated by a distance of 20.0 mm determines the PWV of 8.3 m/sec. The PWV results are summarized in FIG. 5. Note that the right panels in FIG. 5 are for the case when the ultrasound probe is simply reversed along the rubber phantom.

FIG. 5 illustrates measurement of the PWV for the rubber phantom in a longitudinal scan. Right panels are for the second measurement with ultrasound probe reversed. Middle panels show the sharp displacement edge at the onset of systole. Bottom panels are the cross-correlation coefficient of the high pass filtered displacements at the systolic edge. The average time delay of 2.4 msec over the distance of 20.0 mm between red dot 510 and blue dot 520 in the top panels estimates the PWV to be 8.3 m/sec.

Using Eq. (3), the solution for the ratio of (b/a) was determined to be 1.71, resulting in an outer radius of 7.90 mm. Using these numbers for inner and outer radius in Eq. (1), the elastic modulus was reconstructed to be 120.0 kPa.

The phantom was cut into small cylinder for direct mechanical and density measurements. The density was measured to be 815 Kg/m$^3$. The strain-stress curve is produced from the measured force-deformation curve considering the geometry, and is plotted in FIG. 6.

FIG. 6 graphically depicts the stress-strain curve of direct mechanical measurements. Deformation and corresponding force measurements were converted into a stress-strain curve considering the geometry. The slope of the curve determines the elastic modulus. The red curve 610 is the arterial phantom and the blue curve 620 is for the surrounding medium.

At the point where average intramural strain is about 19%, the elastic modulus of the arterial phantom (red curve 610), the slope of the curve, was about 139.0 kPa. Note the elastic modulus of the surrounding soft rubber phantom (blue curve 620) is at least twice as low as that of the arterial phantom at the same average strain and even lower over the lower strain regions. The reconstructed elastic modulus matches well with the direct mechanical measurement with an error of 13%.

Example B

In Vivo Application

To assess the clinical feasibility, in-vivo free-hand ultrasound scanning procedures were performed on two subjects under a study protocol approved by our local investigational review board. The first was a 45 year old healthy male volunteer and the second was a 59 year old with diabetes, hypertension and end stage renal disease on hemodialysis.

The same 12 MHz linear array (L12-5, Philips) used for the ex-vivo experiments was used with continuous freehand compression performed on the surface of the left upper arm close to the brachial artery. To characterize arterial elasticity over a large deformational dynamic range, pressure equalization was also applied, as described herein. While imaging the cross-section of the brachial artery at a rate of 211 frames per second for strain measurements and 411 frames per second for PWV measurements, and collecting ultrasound data frame by frame, surface compression was performed. For the healthy subject, frame rates were 332 frames per second for strain measurements and 287 frames per second for PWV measurements. The applied external force produces internal pressure comparable to that generated in measuring a subject's blood pressure. The compression was increased until the brachial artery pressure exceeded diastolic pressure, as evidenced by viewing B-scan images. An artery pulsates the most when applied external pressure reaches diastolic pressure and the artery collapses when the applied pressure exceeds systolic pressure. This was confirmed with pressure readings when the artery was compressed by a blood pressure cuff. The pulse pressure of each subject was recorded by measuring blood pressure before and after the ultrasound scan. Collected RF data were processed off-line in the same way as described in ex-vivo experiments of Example A.

In-Vivo Scan Measurements

Frame-to-frame displacement of the brachial artery wall was accumulated relative to the original frame. Based on the displacement information depicted in panel (c) in FIGS. 7 and 9, radial normal strain was estimated by taking the spatial derivative.

FIG. 7 shows the intramural strain measurement of the healthy subject after pressure equalization using a transverse scan. (a) B-scan image; (b) correlation coefficient map; (c) accumulated axial displacement from diastole to systole; (d) axial normal strain measurement, the spatial derivative of (c). Note that the transducer is at the top of each image. The average strain on the top and bottom wall over the extended regions marked as boxes was about 40%

For the healthy subject, the inter-cardiac strain estimates 4.1% under physiologic conditions and 36% after pressure equalization (FIG. 7). The pulse pressure (Δp) of the healthy volunteer taken at the time of study was 36 (100/64) mmHg. When the applied pressure matched the internal baseline diastolic pressure (i.e., low preload), strains increased by a factor of 9 with peak strains of 36% over a cardiac cycle (lower right in FIG. 7). By equalizing the baseline arterial pressure to approximate the diastolic pressure, the preload on the arterial wall decreases to zero, resulting in maximal strain. Clearly, the elastic properties of the arterial wall can be better characterized with intramural strain measurements extending over a large preload range.

For the diseased subject, inter-cardiac strain was estimated to be 5% under physiologic conditions and 20% after pressure equalization, shown in FIG. 9.

FIG. 9 shows the intramural strain measurement of the healthy subject after pressure equalization using a transverse scan. (a) B-scan image; (b) correlation coefficient map; (c) accumulated axial displacement from diastole to systole; (d) axial normal strain measurement, the spatial derivative of (c). Note that the transducer is at the top of each image. The average strain on the top and bottom wall over the extended regions marked as boxes was about 20%.

Note the strain was increased only by a factor of 4 compared to the healthy volunteer, indicating arterial hardening. The pulse pressure ($\Delta p$) of the diseased subject taken at the time of study was 90 (180/90) mmHg.

The time delay between two PWV measurement sites was estimated in the same manner as described in Example A for the ex-vivo experiments. The time delay of 0.7 ms under physiologic pressure over 5.7 mm distance determined the PWV to be 8.0 m/s. After pressure equalization the PWV was lowered to 2.7 m/s with a time delay of 2.1 ms (shown in FIG. 8).

FIG. 8 graphically depicts the PWV for the healthy subject after pressure equalization using a longitudinal scan. Right panels are for the second measurement with the ultrasound probe reversed. Middle panels show original displacement over one cardiac cycle. Bottom panels are the cross-correlation coefficient of the high pass filtered displacement at sharp systolic edge. An average time delay of 2.1 msec over the distance of 5.7 mm between red dot 810 and blue dot 820 in the top panels estimates the PWV to be 2.7 m/sec.

Using Eq. (3), the elastic modulus was reconstructed to be 17.1 kPa after pressure equalization and 151 kPa under physiologic pressure. The associated inner and outer radii of the artery were determined to be 1.30 mm and 2.16 mm, respectively, under physiologic condition and 1.29 mm and 2.14 mm, respectively, after pressure equalization.

The same scan and reconstruction procedure were applied to the subject with known vascular disease. The time delay of 1.8 ms under physiologic pressure over 20.4 mm distance determined the PWV to be 11.3 m/s. After pressure equalization the PWV was lowered to 5.7 m/s with a time delay of 3.6 ms (FIG. 10).

FIG. 10 shows the PWV for the healthy subject after pressure equalization: Longitudinal scan. Right panels are for the second measurement with ultrasound probe reversed. Middle panels show original displacement over one cardiac cycle. Bottom panels are the cross-correlation coefficient of the high pass filtered displacement at sharp systolic edge. The average time delay of 3.6 msec over the distance of 20.5 mm between red dot 1010 and blue dot 1020 in the top panels estimates the PWV to be 5.7 m/sec.

Using Eq. (3), the elastic modulus was reconstructed to be 125 kPa after pressure equalization and 468 kPa under physiologic pressure. The associated inner and outer radii of the artery were determined to be 2.13 mm and 3.04 mm, respectively, under physiologic condition and 2.05 mm and 2.74 mm, respectively, after pressure equalization.

Reconstructed elastic moduli were fit to a straight line on a semi-log plot assuming a purely exponential model; i.e., $E=E_o e^{\alpha \epsilon}$, where $\alpha$ is a dimensionless constant describing the degree of nonlinearity. If the elastic modulus of the surrounding tissue can be considered small compared to the arterial elastic modulus, the intercept $E_o$ will determine the undistended (i.e., zero preload) in-vivo arterial elastic modulus. For the normal subject, the intercept $E_o$ ranges from 11.0 kPa to 12.7 kPa (mean±one standard deviation of logarithmic fit), and the slope $\alpha$ is 3.1 with a standard deviation of 0.1. For the diseased subject, the intercept ranges from 105.2 kPa to 134.7 kPa (mean±one standard deviation of logarithmic fit), and the slope $\alpha$ is 4.8 with a standard deviation of 0.5, as graphically depicted in FIG. 11.

FIG. 11 shows the arterial elastic modulus reconstruction over a large deformational dynamic range. The reconstructed elastic moduli were fit to a straight line on the semi-log plot, assuming a purely exponential model; i.e., $E=E_o e^{\alpha \epsilon}$, where $\alpha$ is a dimensionless constant describing the degree of nonlinearity. Open circles are reconstructed moduli and the solid line is the fit for the normal subject (blue 1110). Open squares are reconstructed moduli and the dashed line is the fit for the subject with known vascular disease (red 1120). Note that differences in elastic properties between the two subjects become more pronounced when measured in the low-preload region using pressure equalization.

The ex-vivo and in-vivo results suggest that reconstruction procedures can be used in clinical applications given the quality of intramural strain and PWV measurements produced with multi-dimensional, phase sensitive, ultrasonic speckle tracking. Assessing arterial elasticity may have many important clinical applications. The present teachings allow localized assessment of vascular elasticity that may reflect the degree of both local and general vascular disease. It may be useful in pre-operative assessment for certain vascular surgery procedures, since the elastic properties of the vessel may reflect the capacity of the artery to remodel, influencing clinical outcomes.

For example, in surgically creating an arterial-venous anastomosis in hemodialysis fistula creation, the artery dilates to create a manifold increase in volume flow through the fistula to accommodate hemodialysis, as reported by Konner K, Normast-Daniel B, Ritz E, The arteriovenous fistula, J Am Soc Nephrol. 2003; 14(6):1669-80; and Mills J L, Harris E J, Taylor L M Jr, Beckett W C, Porter J M., "The importance of routine surveillance of distal bypass grafts with duplex scanning: a study of 379 reversed vein grafts", J Vasc Surg. October; 12(4):379-86, 1990. Inelastic, diseased arteries, so prevalent in end stage renal disease, may greatly influence the outcome of the procedure. Assessing the elasticity of arteries preoperatively may favorably influence site selection, prevent the development of peripheral ischemia, and improve clinical outcomes.

Example C

Another In Vivo Application

An optimized elastic modulus reconstruction procedure was developed to estimate the nonlinear elastic properties of the vascular wall from intramural strain and pulse wave velocity (PWV) measurements. A noninvasive free-hand ultrasound scanning procedure was used to apply external force, comparable to the force in measuring a subject's blood pressure, to achieve higher strains by equalizing the internal arterial baseline pressure. PWV was estimated at the same location where intramural strain was measured by simply rotating the ultrasound probe by 90 degrees. The reconstructed elastic modulus was optimized using least squares estimation from two separate measurements. Preliminary in-vivo results demonstrate that arterial elastic modulus can be determined and monitored using a simple dual elastic modulus reconstruction procedure.

In previous studies, a pressure equalization technique was developed to fully characterize nonlinear arterial elastic properties over a large dynamic range. A non-invasive free-hand procedure was performed to apply external force, comparable to the force generated in measuring a subject's blood pressure, to achieve higher strains by equalizing the internal arterial baseline pressure. By lowering preload, it was much easier to differentiate diseased from normal arterial wall. High precision speckle tracking may be able to detect subtle underlying structural changes within the vascular wall and measure corresponding intramural changes in elastic properties with unprecedented resolution, precision, and accuracy. Using a simple geometric model developed in preliminary studies, the arterial elastic modulus was reconstructed. With some uncertainties, including arterial geometrical factors and mechanical boundary conditions, it was demonstrated that this procedure can differentiate a diseased artery from a healthy one. The inner radius of the artery can be relatively easily and accurately determined from the B-Scan and trashogram, but there is more uncertainty in determining the outer arterial boundary surrounded by connective tissues. Geometrical uncertainties in elastic modulus reconstruction can be minimized by employing an independent measurement.

The elastic properties of the arterial wall play an important role in the propagation velocity of the pulse wave. PWV measurement using ECG as a timing reference has been widely used, but it only reflects the average compliance over an extended length; for example, between carotid and femoral. Doppler pulses are recorded sequentially in two different arterial sites and compared using the R-wave of the ECG. The time delay over the estimated length between measurement sites will determine the averaged PWV. Using Tissue Doppler Imaging (TDI), local PWV measurements were attempted. Motion estimation from TDI has two major limitations for precise PWV measurements. First, TDI measurements are inherently Eulerian rather than Lagrangian, which means the same tissue volume is not continually monitored over the cardiac cycle. Second, to avoid aliasing, only very small tissue displacements can be monitored, producing low SNR motion estimates compared to phase-sensitive, cross-correlation speckle tracking. PWV estimation based on speckle tracking will remove these concerns. Using a commercial ultrasound probe, the artery is scanned along the axis of wave propagation. Speckle tracking estimates the time delay between ultrasound beams and this time delay will determine PWV across the known distance between them.

To quantitate arterial compliance independent of geometry and mechanical boundary conditions, the elastic modulus must be reconstructed. Both elastic modulus reconstructions from intramural strain and PWV measurements can be corrupted by inaccurate geometrical factors. Combining these measurements can remove most of the uncertainty, enabling optimized modulus reconstruction by a least squares method. This dual ultrasound technique with pressure equalization may provide a simple and accurate assessment of peripheral vessel compliance, including noninvasive measurements of the carotid artery.

Material and Methods

Human Artery in-vivo. A specially designed RF data acquisition system with ultra high frame rate (up to 500 Hz) was installed on a commercial ultrasound scanner (iU22, Philips, Seattle, Wash.). A 6.8 MHz linear array (L12-5, Philips) was used with continuous freehand compression performed on the surface of the right upper arm close to the brachial artery. While imaging the cross-section of the brachial artery at a rate of about 300 to 400 frames per second and collecting ultrasound data frame by frame, surface compression was performed by the investigators. Only mild compression was applied for the carotid. Compression was increased on the brachial artery until pressure exceeded diastolic pressure, as evidenced by viewing B-Scans.

PWV measurements were also taken in the same area where the transverse scan was performed for intramural strain using the same probe rotated by 90 degrees. A 43 year old healthy male volunteer was scanned. Before and after the study the subject's blood pressure was taken. After the compression ultrasound exam, acquired ultrasound RF data were processed off-line using a phase sensitive, two-dimensional speckle tracking algorithm to determine displacements and time delays.

Optimized Dual Elastic Modulus Reconstruction. In vivo, an artery is connected to surrounding tissue with finite elastic modulus. This means the reconstructed modulus will not be accurate if the finite elasticity of surrounding tissue is ignored. To understand how surrounding tissue can influence elastic modulus reconstruction, a simple model has been used (Appendix 2 in Kim K, Weitzel W. F, Rubin J. M., Xie H., Chen X, O'Donnell M., "Vascular Intramural Strain Imaging Using Arterial Pressure Equalization", Ultrasound in Med. & Biol. 30(6):761-771, 2004) in which surrounding tissue is viewed as a continuous medium with a fixed elastic modulus ($E_2$) and the artery wall is considered homogeneous with a different elastic modulus ($E_1$) while generating intramural strain ($\Delta\epsilon$) due to the pulse pressure ($\Delta p = p_o - p_i$):

$$E_{\mathit{effective}} = E_1 + K_2 E_2 = K_1 \left[ \frac{\Delta p}{\Delta \epsilon} \right], \quad (4)$$

where $$K_1 = \frac{-3a^2 b^2}{2(b^2 - a^2) r^2}, \quad K_2 = \frac{a^2}{(b^2 - a^2)}$$

are geometrical factors computed from B-Scans, $\Delta p$ is the pulse pressure and $\Delta\epsilon$ is inter-cardiac strain (i.e., change in strain from systole to diastole). a is the lumen radius, b is the outer radius of the artery, and r is the intramural strain measurement point. The dimension of the vessel can be determined from both the B-Scan and correlation-based trashogram within an error the size of one half of the speckle spot size (approximately 0.1 mm), representing an estimation error in elastic modulus within 20% if the artery diameter in this study is 3 to 5 mm.

The pulse pressure generated by inter-cardiac blood volume change over the cardiac cycle propagates through the arterial wall. The elasticity of the arterial wall plays an important part in determining the propagation velocity of the pulse wave, as shown in Eq. (5):

$$PWV = \sqrt{\frac{hE}{2 a \rho (1 - v^2)}} = \sqrt{\frac{2hE}{3 a \rho}}, \quad (5)$$

where $\rho$ is density, a is radius, h is thickness, E is elastic modulus and $v$ is Poisson's ratio of the artery, assumed to be ½ for an incompressible medium. Eq. (5), originally derived by Bergel D H. "The dynamic elastic properties of the arterial wall". J. Physiol. 156:458-469, 1961b, represents a modified Moens-Korteweg equation properly accounting for wall thickness.

For the elastic modulus reconstruction procedure described in Eq. (4), two geometrical factors based on values for the inner and outer radius, a and b, are required. The reconstruction procedure from PWV also requires a geometrical factor related to a and b, as described in Eq. (5). The inner radius of the artery can be estimated accurately from B-Scans with the help of the trashogram. The trashogram clearly differentiates the boundary between the inner arterial surface and blood flow inside the lumen. The inner boundary is clearer than the outer boundary in the BScan, however. Also, the trashogram cannot clearly differentiate the outer boundary. Consequently, for real clinical applications there may be substantial error introduced into elastic modulus reconstruction simply from variability in estimates of the outer radius b, and hence the wall thickness.

Assuming that the inner boundary can be estimated with relatively small error, modulus reconstruction generally will require simultaneous estimation of both E and b for robust clinical applications. A least squares estimation technique to simultaneously estimate E and b by combining intramural strain and PWV measurements obtained from ultrasonic speckle tracking is illustrated in FIG. 12. A total error function can be written in terms of the two measurements and two unknowns:

$$\text{Error}=(PMV^{meas}-PMV^{true}(E,b))^2+(\epsilon_r^{meas}-\epsilon_r^{true}(E,b))^2, \quad (6)$$

where $\epsilon_r$ represents radial normal strain. Minimizing this error with respect to the two independent variables, E and b, yields the optimized elastic modulus, $E_O$, and outer radius, $b_O$:

$$\left.\frac{\partial \text{Error}}{\partial E}\right|_{E_O}=0, \quad \left.\frac{\partial \text{Error}}{\partial b}\right|_{b_O}=0. \quad (7)$$

FIG. 12. is a schematic of optimized reconstruction using a least squares method with intramural strain and PWV measurements obtained from transverse and longitudinal scans of an artery. Least squares method is used to solve for E and b.

FIG. 13 illustrates a brachial artery cross section. The inner radius, a, is determined by B-Scan and trashogram to be 1.43 mm and the outer radius was overlaid after the optimized reconstruction process.

Results and Discussion

The intercardiac intramural strain for brachial artery, $\Delta\epsilon$, was 3.1% under physiologic pressure and 40% after pressure equalization. From the BScan and trashogram, the inner radius of the artery (lumen radius) was determined to be 1.43 mm as shown in FIG. 13. The outer circle represents the outer boundary of the artery determined by reconstruction in combination with the PWV measurement. The pulse pressure of the subject at the time of the study was $\Delta p=36(100/64)$ mmHg.

A longitudinal scan was applied to the same spot and the time delay between ultrasound beams separated by a known distance (FIGS. 3 and 4) was measured. The ultrasound probe was then reversed and the time delay measured again. The difference in time delay between these two cases yields the physical delay due to propagation of the pressure pulse.

FIG. 14 illustrates PWV measurement under physiologic pressure. Time delay between known distance from ultrasound beam density determines PWV. (b) is the original pulse waveforms observed at two different locations A and B, and (c) is after high pass filtering. Correlation between high pass filtered signals at two different locations estimates the delay between these two waveforms. To eliminate the delay due to the ultrasound transmitting sequence, the probe was flipped and delay measured in the same manner. The average will result in true travel time.

Using a reasonable initial guess of the outer radius, b, from the B-Scan, iteration was applied to vary the elastic modulus from strain measurement and the outer radius from PWV measurement or vice versa until the error reached a stable minimum. Under physiologic pressure, the iteration converges to the optimized elastic modulus of 302 kPa, and outer radius, b of 2.06 mm. The optimized outer radius is overlaid on the B-Scan in FIG. 13, tracing the outer surface of the artery reasonably. The optimized elastic modulus falls within the numbers found in the literature for this pre-load. After pressure equalization, the iteration converges to the optimized elastic modulus of 25 kPa, and outer radius, b of 2.08 mm. Arterial compliance changes an order of magnitude with pressure equalization. The arterial density involved in the reconstruction procedure from PWV measurements still remains uncertain. According to the literature, it ranges from 1071 to 1100 kg/m^3. Clearly, a simple least squares technique can minimize reconstruction artifacts due to geometrical uncertainties.

FIG. 15 illustrates PWV measurement after pressure equalization. Time delay between known distance determines PWV. (b) and (c) are illustrated in the same way as FIG. 14.

For the carotid artery, only mild compression was applied. The intercardiac intramural strain, $\Delta\epsilon$, was 11% under physiologic pressure. From the B-Scan and trashogram the inner radius of the artery (lumen radius) was determined to be 2.9 mm. The PWV was determined to be 4.7 m/s. The iteration converges to the optimized elastic modulus of 90 kPa, and outer radius, b, of 4.1 mm.

By combining two different ultrasound imaging modalities, the elastic modulus was reconstructed with optimized geometrical parameters. Uncertainty in determining the outer boundary of the artery in vivo was minimized by iteration. A longitudinal PWV scan can be taken at the same location where the transverse intramural strain is estimated using the same ultrasound probe. In combination with pressure equalization, this dual elastic modulus reconstruction procedure will determine the local nonlinear arterial elastic characteristics relatively easily with high precision. Preliminary in-vivo measurements suggest that even small local changes in arterial stiffness accompanying vascular disease such as arterial plaques may be accurately localized and sensitively monitored by dual elastic modulus reconstruction.

Example D

Local Nonlinear Arterial Elastic Modulus Reconstruction from In Vivo Strain Imaging and PWV An optimized elastic modulus reconstruction procedure from ultrasound strain and pulse wave velocity (PWV) measurements was validated using a commercial ultrasound scanner. Longitudinal and transverse scans were performed on a vessel phantom connected to a pulsatile pump. Time delay between the ultrasound beams at each side of the transducer determines PWV and transverse elasticity imaging estimates intramural strain. Elastic modulus was reconstructed combining these two independent measurements. The reconstructed elastic modulus compared well to the direct mechanical measurement within 10% error. To assess clinical feasibility, an in vivo free-hand ultrasound scanning procedure was performed on a local vein graft at anastomosis of a recruited subject under IRB approval. Transverse and longitudinal scanning was performed on the vein side of the anastomosis while compressing to a pressure equaling diastolic pressure, to achieve higher strains by equalizing the internal arterial baseline pressure. Elastic moduli with and without compression were fit to a pure exponential function describing the nonlinear elasticity of the arterial wall. With only two measurement points at different intraluminal pressures, the vein elastic property was fully characterized demonstrating the feasibility of determining the un-distended elastic modulus in vivo.

To quantitate blood vessel compliance independent of geometry and mechanical boundary conditions, the elastic modulus needs to be reconstructed. Using a simple geometry model developed in the previous studies [Kim K, Weitzel W. F, Rubin J. M., Xie H., Chen X, O'Donnell M., "Vascular Intramural Strain Imaging Using Arterial Pressure Equalization", Ultrasound in Med. & Biol. 30(6):761-771, 2004], the arterial elastic modulus was able to be reconstructed. With some uncertainties, including arterial geometry factors and mechanical boundary conditions, it was demonstrated that this reconstruction procedure can differentiate a diseased artery from a healthy one [Kim K, Weitzel W. F, Rubin J. M., Xie H., Chen X, O'Donnell M., "Vascular Intramural Strain Imaging Using Arterial Pressure Equalization", Ultrasound in Med. & Biol. 30(6):761-771, 2004; and W. F. Weitzel, K. Kim, J. M. Rubin, H. Xie, and M. O'Donnell, "Renal Advances in Ultrasound Elasticity Imaging: Measuring the Compliance of Arteries and Kidneys in End-Stage Renal Disease," Blood Purification, vol. 23, pp 10-17, (2005)]. The inner radius of the artery can be relatively easily and accurately determined from B-scan image and trashogram, but there is more uncertainty in determining outer boundary of the artery surrounded by the connective tissues. In the previous study [K. Kim, W. F. Weitzel, Hua Xie, J. M. Rubin, Congxian Jia, M. O'Donnell, "Dual Arterial Elastic Modulus Reconstruction from In-vivo Strain Imaging and PWV" Proc. IEEE International Ultrasonics Symposium, 381-384, 2005], it was proposed that geometrical uncertainties in elastic modulus reconstruction procedure can be minimized by employing an independent measurement.

Vessel PWV also reflects vessel compliance. Conventional PWV measurement techniques only provides average velocity over the extended length of the artery [Asmar R, Benetos A, Topouchian J, Laurent P, Pannier B, Brisac A M, Target R, Levy B I., "Assessment of arterial distensibility by automatic pulse wave velocity measurement. Validation and clinical application studies.", Hypertension, 26(3):485-90, 1995.], or limited to small tissue displacement and Eulerian measurements [Eriksson A, Greiff E, Loupas T, Persson M, Pesque P. Arterial pulse wave velocity with tissue Doppler imaging. Ultrasound in Med. & Biol. 2002; vol. 28: No. 5:571-580]. To assess local elastic property change, Local PWV estimation by measuring time delay between ultrasound beams along the vessel was proposed and applied to in-vivo study [K. Kim, W. F. Weitzel, Hua Xie, J. M. Rubin, Congxian Jia, M. O'Donnell, "Dual Arterial Elastic Modulus Reconstruction from In-vivo Strain Imaging and PWV" Proc. IEEE International Ultrasonics Symposium, 381-384, 2005].

An optimized elastic modulus reconstruction procedure from ultrasound strain and pulse wave velocity (PWV) measurements, proposed in the previous study [K. Kim, W. F. Weitzel, Hua Xie, J. M. Rubin, Congxian Jia, M. O'Donnell, "Dual Arterial Elastic Modulus Reconstruction from In-vivo Strain Imaging and PWV" Proc. IEEE International Ultrasonics Symposium, 381-384, 2005], was validated using a commercial ultrasound scanner. To assess clinical feasibility, an in vivo free-hand ultrasound scanning procedure was performed on a local vein graft at anastomosis of a recruited subject, under IRB approval, with an artery-vein bypass.

Material and Methods

Pulsatile System with Vessel Phantom. A cylindrical rubber phantom seeded with 0.4% by weight polystyrene spheres (Amberlite, Sigma Chemical Co., MO) was constructed for the experiments. The phantom was over 300 mm long, 15.9 mm in diameter, and had an inner lumen 9.2 mm in diameter. To avoid any undesired translational motion, the artery phantom was embedded in a soft rubber phantom block; there were no ultrasound scatterers in this block. It was soft and large enough to minimize any boundary effects (over 100 mm by 100 mm by 300 mm). The artery phantom was connected to a pulsatile pump (Model 553305, Harvard Apparatus, Holliston, Mass.) acting as the pulse pressure source. Internal cyclic pressure was monitored and recorded using a pressure sensor (P-15PSIG-D/5P, Alicat Scientific Inc., Tucson, Ariz.), connected into lumen about 30 mm away from the ultrasound measurement site. The pulsatile pump was set with 15 cc/stroke, 20 rpm, and 25/75 for systole/diastole ratio for intramural strain measurement.

Local PWV estimation using near parallel M-mode. A special pulse/receiving sequence close to a parallel M-mode with ultra high frame rate (3571.4 Hz) was installed on a commercial ultrasound scanner (Sonix RP, Ultrasonix, BC, Canada). A 14 MHz linear array (Sonix RP, Ultrasonix, BC, Canada) was positioned along the vessel. Two ultrasound beam groups on each side of the transducer were sequentially fired (FIG. 16). Each ultrasound beam group consists of two beams. To generate a relatively short pulse wave, one end of the phantom connected to a syringe was instantly hammered while the other end was open. The develop peak intraluminal pressure was measured to be 140 mmHg. The time delay between beams was set to be 70 microseconds to cover the imaging depth of 35 mm. RF data from every frame in the sequence were captured. Data were subsequently processed using phase-sensitive, speckle-tracking to determine intramural displacements. The sharp edge corresponding to the start of systole was high-pass filtered. The filtered signals from each side were then cross-correlated to determine the time delay.

FIG. 16 illustrates near parallel M-mode for PWV. The numbers indicate the pulse/receiving sequence. $t_A$ and $t_B$ are pulse wave arrival times on corresponding site and $\Delta t_{beam}$ is the time delay between beams.

Intramural Strain Estimation.

While the arterial phantom undergoes cyclic deformation, the same linear ultrasound array (Sonix RP, Ultrasonix, BC, Canada) used for PWV measurement imaged the cross section along the short axis of the phantom at a rate of 113.3 frames per second for about 1.3 seconds. The full set of 128 ultrasound beams was operated. RF data from every frame in the sequence were captured. The intraluminal pressure over time was also recorded. Data were subsequently processed using phase-sensitive, two-dimensional speckle-tracking to determine intramural displacements and strains [Lubinski M A, Emelianov S Y, O'Donnell M, "Speckle tracking methods for ultrasonic elasticity imaging using short time correlation", IEEE Transactions on Ultrasonics, Ferroelectrics, and Frequency Control 46:82-96, 1999]. Frame-to-frame displacement estimates were integrated from and registered to the initial coordinate system. Spatial derivatives of the displacements were computed in one region of the artery to estimate the radial normal strain. The recorded pulse pressure was used for elastic modulus reconstruction.

In-Vivo Measurements

To assess clinical feasibility, an in vivo free-hand ultrasound scanning procedure was performed on a local vein graft at anastomosis of a recruited subject, under IRB approval, with a artery-vein bypass. Transverse and longitudinal scanning was performed on the vein side of the anastomosis while compressing to a pressure equaling diastolic pressure.

A specially designed RF collecting system with ultra high frame rate (up to 500 Hz) for transverse intramural strain and PWV measurements was installed on a commercial ultrasound scanner (iU22, Philips, Seattle, Wash.). A 12 MHz linear array (L12-5, Philips) was used with continuous free-hand compression performed on the surface of the right upper arm close to the brachial artery. While imaging the cross-section of the brachial artery at a rate of 203 frames per second and collecting ultrasound data frame by frame, surface compression was performed by the investigators.

PWV measurements were also taken at the same area where transverse scan was performed for the intramural strain using the same probe rotated by 90 degrees. Before and after the study the blood pressure of the subject was taken.

Optimized Dual Elastic Modulus Reconstruction

A simple model, assuming incompressibility, plane strain in the cross-section of the artery phantom, and small effects by soft surrounding material, relates elastic modulus E of the artery wall to pulse pressure ($\Delta p$) and inter-cardiac strain ($\Delta \epsilon$) by $$E = K\left[\frac{\Delta p}{\Delta \epsilon}\right],$$

where $$K = \frac{-3a^2 b^2}{2(b^2 - a^2)r^2},$$

a is the lumen radius, b is outer radius of the artery, and r is the strain measurement point [1]. The pulse pressure generated by inter-cardiac blood volume change over the cardiac cycle propagates through the arterial wall. The elastic property of the arterial wall plays an important part in determining the propagation velocity of the pulse wave, as shown in Eq. (9):

$$PWV = \sqrt{\frac{hE}{2a\rho(1-v^2)}} = \sqrt{\frac{2hE}{3a\rho}}, \quad (9)$$

where $\rho$ is density, a is radius, h is thickness, E is elastic modulus and $v$ is Poisson's ratio of the artery, assumed to be ½ for an incompressible medium. Eq. (9), originally derived by Bergel D H. "The dynamic elastic properties of the arterial wall". J. Physiol. 156:458-469, 1961b, represents a modified Moens-Korteweg equation properly accounting for wall thickness. In both cases, artery geometrical factors, including inner and outer radius, must be determined. Arterial inner radius, a, can be measured from B-scan and correlation maps at relatively high accuracy. Combining these two equations leads to the equation for the ratio of outer radius to inner radius (b/a):

$$\left(\frac{\Delta p}{\Delta \epsilon}\right) \frac{\left(\frac{b}{a}\right)^2}{\left[\left(\frac{b}{a}\right)+1\right]^3} = \left(\frac{\rho}{4}\right) PWV^2. \quad (10)$$

Out of three possible solutions for (b/a), only one positive and real solution greater than unity is taken. In the case where there are more than one real solution greater than unity, the smallest value should be taken to satisfy the assumption that the wall is sufficiently thin so that the inertia can be neglected in comparison with that of fluid [King A L. "Waves in elastic tube: Velocity of the pulse wave in large arteries". J. Applied Physics Vol. 18, 595-600, 1947]. For the ex-vivo experiment, the density, $\rho$, was measured and for the in-vivo scan, the nominal value for arterial tissue (1071-1100 Kg/m$^3$) was used. Once b is obtained, the elastic modulus can be determined either from Eq. (8) or Eq. (9).

Direct Mechanical Measurement

A mechanical system developed in our laboratory was used [Erkamp R Q, Wiggins P, Skovoroda A R, Emelianov S Y, O'Donnell M, "Measuring the Elastic Modulus of Small Tissue Samples," Ultrasonic Imaging 20:17-28, 1998]. The same rubber phantom used for ultrasound strain and PWV measurements was cut into a small cylindrical piece to fit into the sample holder. The strain and simultaneously measured resulting force under conditions of continuous deformation applied to the sample were used to determine the elastic modulus.

Results and Discussion

The pulse wave M-modes of the top wall at each side of the transducer, corresponding to the geometry in FIG. 16, are presented in FIG. 17 (a). The displacement at the midpoint of the wall thickness is depicted in FIG. 17 (b). The sharp edge at the onset of systole was high pass filtered to accurately determine the time delay between two measurement sites FIG. 17 (c).

The correlation between filtered signals resulted in a time delay of 3.3 ms, taking into account of 0.07 ms of time delay between two beams. This time delay of 3.3 ms due to the pulse wave traveling time between two beams separated by a distance of 28.5 mm determines the PWV of 8.7 m/sec FIG. 17 illustrates PWV measurement on a rubber phantom.

The average intramural inter-cardiac strain from transverse scan was about 21% (FIG. 18). The axial displacement is presented over a −3 mm to +3 mm range in FIG. 18 (a). Blue 1820 represents motion toward the transducer and red 1830 represents motion away from the transducer for this display. The strain was averaged over the extended region of the top and bottom wall as marked 1810 in the FIG. 18. Artifacts around inside and outside boundaries were ignored. The pulse pressure was measured to be 165 mmHg.

Using Eq. (10), the solution for the ratio of (b/a) was determined to be 1.74, resulting in an outer radius of 8.1 mm. The inner and outer radius of artery phantom, a and b, were determined to be 4.62 mm and 7.95 mm respectively both from B-scan and trashogram. Using these numbers for inner and outer radius in Eq. (1), the elastic modulus was reconstructed to be 124.0 kPa. The elastic modulus from the direct mechanical measurement was 139.0 kPa at about 21% preloading.

FIG. 18 illustrates transverse scanning for strain measurement: (a) axial displacement, (b) axial strain.

The intramural inter-cardiac intramural strain for vein graft, $\Delta \epsilon$, was 15% under physiologic pressure and 65% after pressure equalization. From the B-scan image and trashogram the inner radius of the artery (lumen radius) was determined to be 2.3 mm under physiologic pressure and 2.0 mm after pressure equalization. The pulse pressure of the subject at the time of the study was Δp=44(120/76)mmHg.

A longitudinal scan was applied to the same spot and the time delay between the ultrasound beams separated by a known distance (FIG. 19) was measured. The ultrasound probe was then reversed along the artery and the time delay between ultrasound beams measured again. The average in time delay between these two cases will result in the physical delay due to propagation of the pressure pulse. PWV was 4.3 m/s under physiologic pressure. After pressure equalization the PWV was 1.7 m/s.

FIG. 19 illustrates PWV measurement after pressure equalization. Time delay between known distance from ultrasound beam density determines PWV. (b) is the original pulse wave forms observed at two different locations A and B, and (c) is after high pass filter FIG. 20 illustrates elastic modulus reconstruction over full dynamic range.

Using the elastic modulus reconstruction procedure proposed in the Method section, the elastic moduli with and without compression were fit to a straight line as illustrate in the left panel in FIG. 20. The slope was 3.1 and undistended vein elastic modulus was estimated to be 7.2 kPa. With only two measurement points with and without compression, the nonlinear elastic property of the vein was fully characterized to determine the undistended elastic modulus in-vivo. The pulse pressure on the vein near anastomosis was high enough to apply pressure equalization technique.

By combining two independent ultrasound imaging modalities, the elastic modulus of a peripheral wall was reconstructed with optimized geometric parameters. A simple procedure was developed and tested ex-vivo and applied to an in-vivo study. A longitudinal PWV scan can be taken at the same location where the transverse intramural strain is estimated using the same ultrasound probe. In combination with pressure equalization, this dual elastic modulus reconstruction procedure will determine the local nonlinear arterial elastic characteristics, especially the undistended (i.e., zero preload) in-vivo arterial elastic modulus, relatively easily with high precision. Preliminary in-vivo results support the potential of clinical application.

The present teachings include an elastic modulus reconstruction procedure. Pressure equalization combined with ultrasonic speckle tracking provides a local, direct, sensitive, accurate, and precise assessment of peripheral arterial compliance. This reconstruction procedure can determine the undistended (i.e., zero preload) in-vivo arterial elastic modulus.

The description of the technology is merely exemplary in nature and, thus, variations that do not depart from the gist of the present disclosure are intended to be within the scope of the invention. Such variations are not to be regarded as a departure from the spirit and scope of the invention.

What is claimed is:

1. A method of monitoring vascular wall compliance comprising:
   measuring pulse wave velocity of the vascular wall over two or more mechanical loads from systolic pressure to equalized pressure;
   measuring intramural strain of the vascular wall over two or more mechanical loads from systolic pressure to equalized pressure; and
   reconstructing an elastic modulus for the vascular wall using the intramural strain and pulse wave velocity;
   wherein the steps of measuring pulse wave velocity and measuring intramural strain each utilize an ultrasound probe and measuring pulse wave velocity comprises estimating the pulse wave velocity from a time delay between two ultrasound beams separated by a known distance.

2. The method of monitoring vascular wall compliance according to claim 1, wherein measuring pulse wave velocity includes rotating the ultrasound probe about 90 degrees relative to measuring intramural strain.

3. The method of monitoring vascular wall compliance according to claim 1, wherein measuring pulse wave velocity includes longitudinal ultrasound scanning of the vascular wall.

4. The method of monitoring vascular wall compliance according to claim 3, wherein the longitudinal ultrasound scanning spans from about 1 centimeter to about 10 centimeters.

5. The method of monitoring vascular wall compliance according to claim 1, wherein the time delay is based on a first arrival part of an ultrasound wave.

6. The method of monitoring vascular wall compliance according to claim 1, wherein the time delay is determined using speckle tracking to trace a frame-to-frame intramural wall displacement on each ultrasound beam.

7. The method of monitoring vascular wall compliance according to claim 3, wherein longitudinal ultrasound scanning of the vascular wall includes a plurality of measurements.

8. The method of monitoring vascular wall compliance according to claim 1, wherein measuring intramural strain includes transverse ultrasound scanning of the vascular wall.

9. The method of monitoring vascular wall compliance according to claim 1, wherein measuring intramural strain includes using phase-sensitive, two-dimensional speckle-tracking to determine intramural displacement and strain.

10. The method of monitoring vascular wall compliance according to claim 1, wherein reconstructing an elastic modulus for the vascular wall using the intramural strain and pulse wave velocity includes:
    measuring an inner radius of the vascular wall;
    determining an outer radius using the pulse wave velocity and the inner radius; and
    ascertaining the elastic modulus of the vascular wall based on:
      (a) the inner and outer radii, pulse pressure, and inter-cardiac strain, or
      (b) the inner and outer radii and the density of the vascular wall.

11. A system for determining the vascular health of a patient comprising:
    means for measuring pulse wave velocity of a vascular wall over two or more mechanical loads from systolic pressure to equalized pressure, wherein the means for measuring pulse wave velocity includes means for estimating the pulse wave velocity from a time delay between two ultrasound beams;
    means for measuring intramural strain of the vascular wall over two or more mechanical loads from systolic pressure to equalized pressure;
    means for reconstructing an elastic modulus of the vascular wall using the intramural strain and pulse wave velocity measurements; and
    means for comparing the reconstructed elastic modulus to the elastic moduli of diseased and healthy vascular wall.

12. The system for determining the vascular health of a patient according to claim 11, wherein means for measuring intramural strain includes means for transverse ultrasound scanning of the vascular wall.

13. A method for locating a vascular wall lesion comprising:
  measuring pulse wave velocity by longitudinal ultrasound scanning of the vascular wall over two or more mechanical loads from systolic pressure to equalized pressure, the longitudinal ultrasound scanning having proximal and distal ends, and estimating the pulse wave velocity from a time delay between two ultrasound beams separated by a known distance; and
  locating the vascular wall lesion by comparing the pulse wave velocity at proximal and distal ends of the longitudinal scan.

14. The method for locating a vascular wall lesion according to claim 13, wherein measuring pulse wave velocity by longitudinal ultrasound scanning of the vascular wall includes measuring pulse wave velocity at a plurality of points along the longitudinal axis.

15. The method for locating a vascular wall lesion according to claim 13, wherein the longitudinal ultrasound scanning spans from about 1 centimeter to about 10 centimeters.

16. The method for locating a vascular wall lesion according to claim 13, wherein the time delay is based on a first arrival part of an ultrasound wave.

17. The method for locating a vascular wall lesion according to claim 13, wherein the time delay is determined using speckle tracking to trace a frame-to-frame intramural wall displacement on each ultrasound beam.

18. The method of monitoring vascular wall compliance according to claim 1, further comprising measuring blood pressure.

* * * * *